(12) United States Patent
Jung et al.

(10) Patent No.: US 10,248,202 B2
(45) Date of Patent: Apr. 2, 2019

(54) VIDEO DISPLAY APPARATUS AND METHOD FOR REDUCING VR SICKNESS

(71) Applicant: SAMSUNG ELECTRONICS CO., LTD., Suwon-si (KR)

(72) Inventors: Hyun-ki Jung, Seoul (KR); Hyun-ki Kim, Suwon-si (KR); Jae-min Moon, Seoul (KR); Chi-yul Yoon, Hwaseong-si (KR); Sang-min Lee, Hwaseong-si (KR); Seong-hyun Jang, Seoul (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 11 days.

(21) Appl. No.: 15/396,942

(22) Filed: Jan. 3, 2017

(65) Prior Publication Data
US 2017/0249010 A1    Aug. 31, 2017

(30) Foreign Application Priority Data

Feb. 29, 2016 (KR) .................. 10-2016-0024301
Aug. 22, 2016 (KR) .................. 10-2016-0106171

(51) Int. Cl.
*G06F 3/01* (2006.01)
*A61N 1/36* (2006.01)

(52) U.S. Cl.
CPC ............ *G06F 3/015* (2013.01); *A61N 1/36* (2013.01); *A61N 1/36036* (2017.08); *G06F 3/011* (2013.01); *G06F 3/012* (2013.01); *G06F 3/016* (2013.01); *G06F 3/017* (2013.01)

(58) Field of Classification Search
CPC .......... G06F 3/015; G06F 3/012; G06F 3/017; G06F 3/016; G06F 3/011; A61N 1/36; A61N 1/36036
See application file for complete search history.

(56) References Cited

U.S. PATENT DOCUMENTS

| | | | | |
|---|---|---|---|---|
| 8,718,796 B2* | 5/2014 | Cevette | ............... | G09B 9/00 607/139 |
| 9,999,835 B2* | 6/2018 | Watson | ............... | G06F 3/013 |
| 2011/0044604 A1* | 2/2011 | Brokken | ............... | G06F 3/016 386/239 |

(Continued)

FOREIGN PATENT DOCUMENTS

| KR | 10-2010-0130620 A | 12/2010 |
|---|---|---|
| KR | 10-1564964 B1 | 11/2015 |

(Continued)

OTHER PUBLICATIONS

International Search Report and Written Opinion, issued by International Searching Authority in corresponding International Application No. PCT/KR2016/014978, dated Mar. 28, 2017, (PCT/ISA/220, PCT/ISA/210 & PCT/ISA/237).

(Continued)

*Primary Examiner* — Catherine M Voorhees
(74) *Attorney, Agent, or Firm* — Sughrue Mion, PLLC

(57) ABSTRACT

A video display apparatus includes a display configured to reproduce a video, a processor configured to generate a signal for applying an electrical stimulus to a user, based on a motion depicted in the video, and a communication unit configured to transmit the signal to an electrical stimulation apparatus.

15 Claims, 24 Drawing Sheets

VIDEO OF FIRST-PERSON VIEWPOINT

TRANSMIT SIGNAL

ELECTRICAL STIMULUS

VIDEO OF THIRD-PERSON VIEWPOINT

SIGNAL IS NOT TRANSMITTED OR ELECTRICAL STIMULUS IS NOT APPLIED

(56) References Cited

U.S. PATENT DOCUMENTS

| | | |
|---|---|---|
| 2012/0036004 A1 | 2/2012 | Pradeep et al. |
| 2012/0050143 A1 | 3/2012 | Border et al. |
| 2015/0325027 A1* | 11/2015 | Herman .................. G06T 13/00 345/633 |
| 2016/0158544 A1* | 6/2016 | Guarraia .................. A61N 1/36 607/63 |

FOREIGN PATENT DOCUMENTS

| | | | |
|---|---|---|---|
| KR | 10-2016-0007957 A | | 1/2016 |
| WO | WO 2016126110 | * | 8/2016 |

OTHER PUBLICATIONS

Aoyama, et al.; "Four-Pole Galvanic Vestibular Stimulation Causes Body Sway About Three Axes", Scientific Reports, May 2015, 8 pages total.

Communication dated Sep. 19, 2018 issued by the European Patent Office in Counterpart European Application No. 16892808.3.

Maiti et al., "Estimation of Round Trip Time in Distributed Real Time System Architectures", 2013 Australasian Telecommunication Networks and Applications Conference (ATNAC), IEEE, Nov. 2013, pp. 57-62, XP032543067.

Gámez et al., "Wireless Network Delay Estimation for Time-Sensitive Applications", Jul. 27, 2006, pp. 1-13, XP055394251.

* cited by examiner

FIG. 9
ELECTRICAL STIMULUS FOR GENERAL MOTION
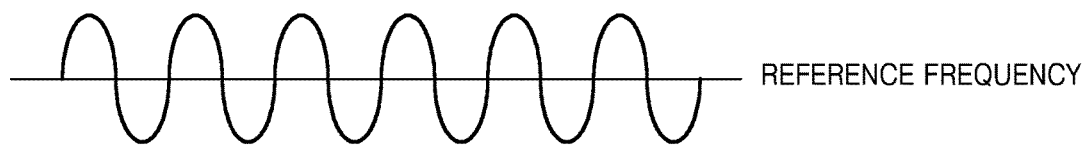
— REFERENCE FREQUENCY
<FREQUENCY IS ADJUSTED>
ELECTRICAL STIMULUS FOR SMALL MOTION
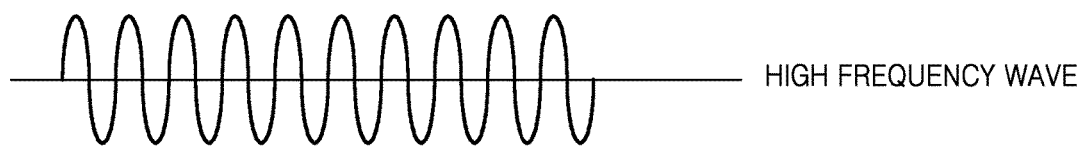
— HIGH FREQUENCY WAVE FIG. 10
ELECTRICAL STIMULUS FOR VIDEO ROTATING LEFTWARDS
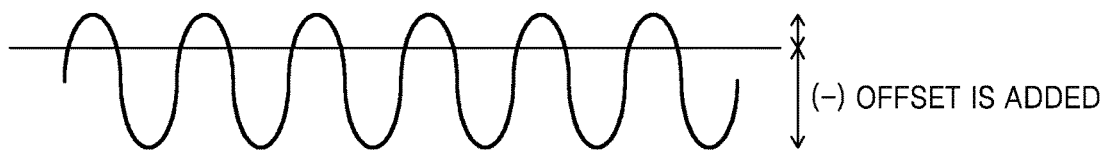
(−) OFFSET IS ADDED
ELECTRICAL STIMULUS FOR VIDEO ROTATING RIGHTWARDS
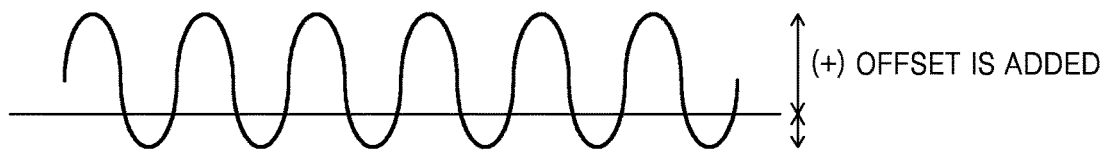
(+) OFFSET IS ADDED

<ADJUST INTENSITY OF ELECTRICAL STIMULUS>

FIG. 20

| NAME | VALUE |
|---|---|
| TIME | TIME AT WHICH ELECTRICAL STIMULUS IS APPLIED |
| TYPE | TYPES OF ELECTRICAL STIMULI<br>1. PITCH<br>2. ROLL<br>3. YAW |
| MODE | WAVEFORM<br>1. DCS (DC CURRENT)<br>2. ACS (AC CURRENT)<br>3. CUSTOM MOTION TYPE (USER SPECIFIC) |
| CURRENT | 0 ~ 2.0 mA |
| FREQUENCY | 0 ~ 60 Hz |
| COUNT | NUMBER OF REPETITIONS 0.1 ~ 655 |
| DIRECTION | UP<br>LEFT<br>RIGHT<br>DOWN |

VIDEO DISPLAY APPARATUS AND METHOD FOR REDUCING VR SICKNESS

CROSS-REFERENCE TO RELATED APPLICATIONS

This application claims priority from Korean Patent Application No. 10-2016-0024301, filed on Feb. 29, 2016, and Korean Patent Application No. 10-2016-0106171, filed on Aug. 22, 2016, in the Korean Intellectual Property Office, the disclosures of which are incorporated herein by reference in their respective entireties.

BACKGROUND

1. Field

Exemplary embodiments relate to a video display apparatus and a method for reducing virtual reality (VR) sickness.

2. Description of the Related Art

The user may view a video obtained by photographing a three-dimensional (3D) space by using a video display apparatus while a virtual reality (VR) device is mounted on the head of the user. The user may rotate his or her head while watching the video, and the video display apparatus reproduces the video in a manner that varies based on a direction of the head.

While the user watches content such as a movie, a drama, or sports, an odor or a motion may be provided based on the content. The motion may be provided by directly moving a chair on which the user is seated, or may be provided by applying a current to the user to enable the user to feel as if he or she is moving.

SUMMARY

Provided are a video display apparatus and a method for reducing virtual reality (VR) sickness of a user.

Provided are a video display apparatus and a method for enhancing a user's sense of reality.

Provided is a non-transitory computer-readable recording medium in which a program for executing the method by a computer is recorded.

Additional aspects will be set forth in part in the description which follows and, in part, will be apparent from the description, or may be learned by practice of the presented exemplary embodiments.

According to an aspect of an exemplary embodiment, a video display apparatus includes a display configured to reproduce a virtual reality video, a processor configured to generate a signal for applying an electrical stimulus to a user based on a motion depicted in the video, and a communicator configured to transmit the generated signal to an electrical stimulation apparatus.

BRIEF DESCRIPTION OF THE DRAWINGS

These and/or other aspects will become apparent and more readily appreciated from the following description of exemplary embodiments, taken in conjunction with the accompanying drawings in which:

FIG. 9 is a graph for explaining an example of adjusting frequency based on a degree of change in a video, according to an exemplary embodiment;

FIG. 10 is a graph for explaining an example of adding an offset based on a rotational direction of a video;

FIG. 20 is a table illustrating an example of electrical stimulus data representing video information;

DETAILED DESCRIPTION

Figure 1:
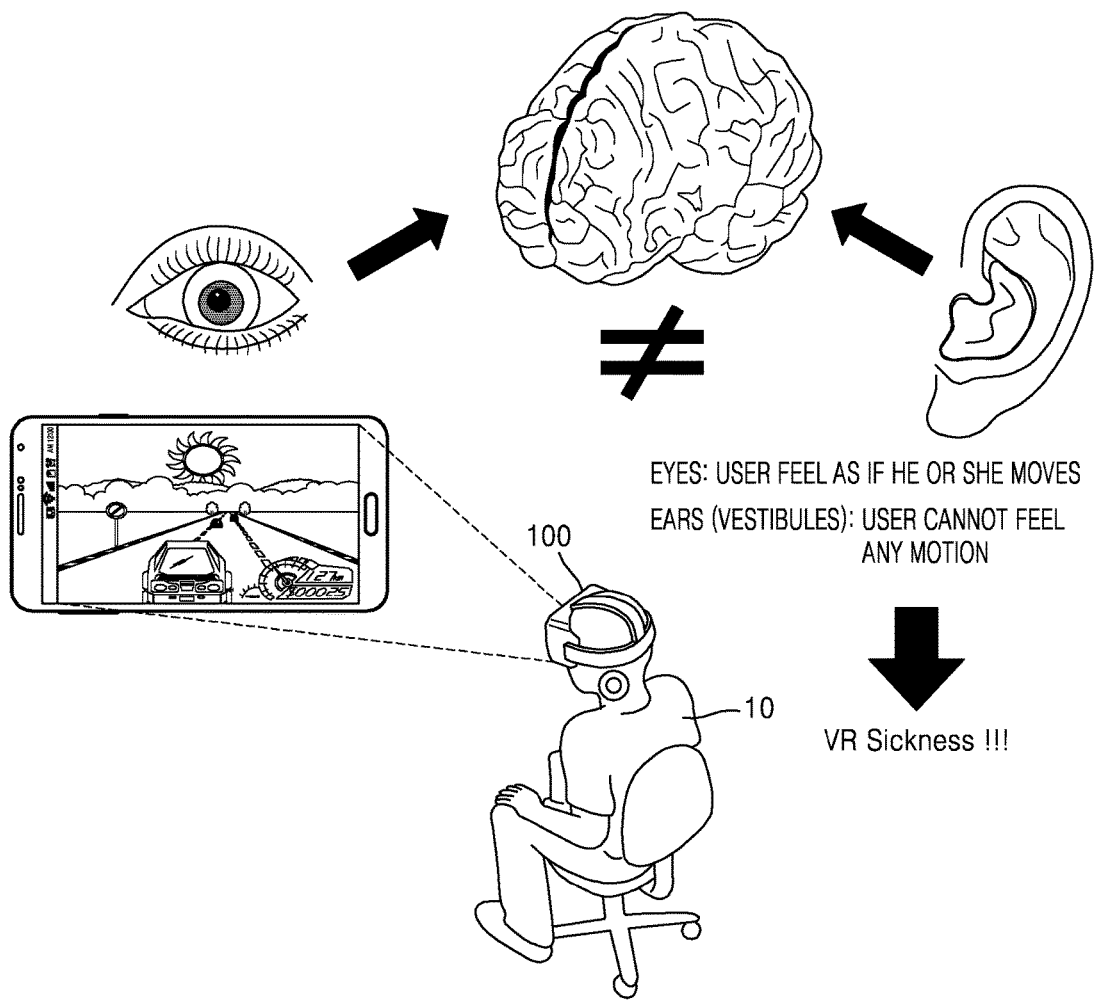
FIG. 1 is a diagram for explaining a cause of virtual reality (VR) sickness.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects thereof.

Hereinafter, the exemplary embodiments will be described in detail with reference to the accompanying drawings.

FIG. 1 is a diagram for explaining a cause of virtual reality (VR) sickness. The user 10 watches a video via a video display apparatus 100. The video display apparatus 100 reproduces a video such that the user feels like he or she is in a virtual reality. Because the eyes of the user view the video, the user 10 feels as if he or she is moving. However, because the user 10 does not move in reality, his or her vestibular system fails to recognize any motion, and he or she may feel sickness due to the difference between the virtual motion and the lack of recognition of motion by the vestibular system. Accordingly, the user 10 may be prevented from feeling sickness by applying an electrical stimulus to the vestibular system.

Figure 2:
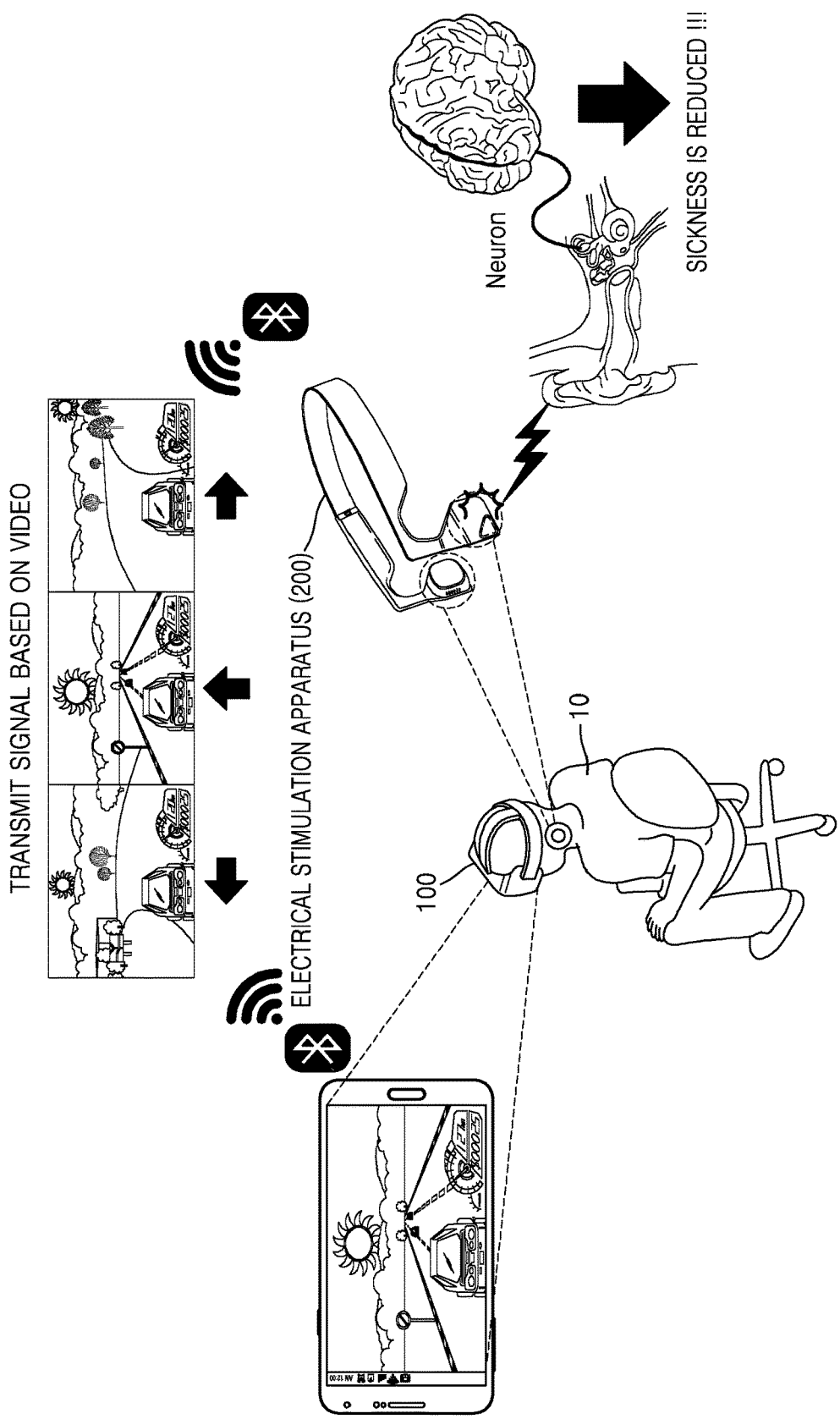
FIG. 2 is a diagram illustrating an exemplary embodiment for reducing VR sickness of a user.

FIG. 2 is a diagram illustrating an exemplary embodiment for reducing VR sickness of the user. Referring to FIG. 2, the video display apparatus 100 may control an electrical stimulation apparatus 200 such that an electrical stimulus is applied to the user 10 by transmitting a signal to the electrical stimulation apparatus 200.

The user 10 watches a video through the video display apparatus 100. The user 10 may also wear the electrical stimulation apparatus 200. The electrical stimulation apparatus 200 may be an apparatus that is separate from the video display apparatus 100. The electrical stimulation apparatus 200 and the video display apparatus 100 may be integrally manufactured, for example, in the form of a head mounted display (HMD).

The video display apparatus 100 analyzes a video and transmits a signal based on the video to the electrical stimulation apparatus 200. The video display apparatus 100 detects a viewpoint of a video, a directional change in the video, a degree of change of the video, and the like, and transmits a signal to the electrical stimulation apparatus 200. The video display apparatus 100 transmits a signal for controlling a magnitude, a frequency, an offset, and the like of an electrical stimulation to the electrical stimulation apparatus 200. The forms of the electrical stimulus will be described in detail below with reference to FIGS. 9, 10, and 11.

The electrical stimulation apparatus 200 applies an electrical stimulus to the user 10 based on the signal received from the video display apparatus 100. For example, the electrical stimulation apparatus 200 may apply a current to the user 10. The electrical stimulation apparatus 200 adjusts the intensity, the frequency, the offset, and the like of the electrical stimulus based on the signal received from the video display apparatus 100, and applies the adjusted electrical stimulus to the user 10.

The vestibular system of the user 10 reacts in response to the electrical stimulus and a signal is delivered to the brain via neurons. Accordingly, the user 10 feels less sickness if an electrical stimulus is applied, as compared with the case in which an electrical stimulus is not applied.

Figure 3:
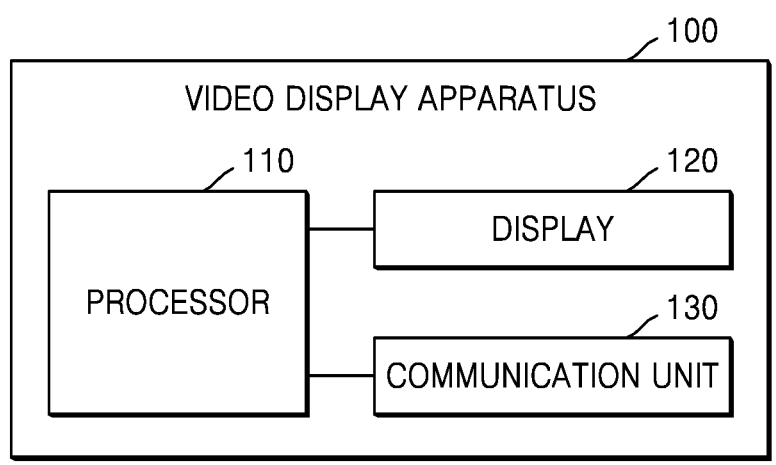
FIG. 3 is a block diagram of a video display apparatus, according to an exemplary embodiment.

FIG. 3 is a block diagram of a video display apparatus, according to an exemplary embodiment. Referring to FIG. 3, the video display apparatus 100 includes a processor 110, a display 120, and a communication unit (also referred to herein as a "communicator" and/or as a "transceiver") 130.

The processor 110 controls the display 120 and the communication unit 130. The processor 110 controls the display such that the display 120 displays a video, by providing the video to the display 120. The processor 110 transmits a signal to the electrical stimulation apparatus 200 via the communication unit 130.

The processor 110 analyzes a video in order to extract a feature of the video. The processor 110 determines a viewpoint of the video. A viewpoint of a video may refer to a viewpoint of the user who views the video. For example, the processor 100 may determine whether a viewpoint of the video is a first-person viewpoint or a third-person viewpoint. Further, the processor 110 may determine whether the viewpoint of the video is a combination of a first-person viewpoint and a third-person viewpoint. A video of a first-person viewpoint is defined herein as a video captured from a viewpoint of an object situated in a three-dimensional (3D) space, and a third-person viewpoint is defined herein as a video captured from the outside of an object. In particular, a video of a first-person viewpoint is a video of a 3D space, in which the 3D space is viewed from the viewpoint of an object, and a video of a third-person viewpoint is a video of a 3D space, in which the 3D space is viewed from the outside. Further, the video may be changed from a first-person viewpoint to a third-person viewpoint or vice versa. The processor 110 determines a background or a motion of an object depicted in the video. The processor 110 may determine a viewpoint of the video by determining whether the background moves or the object moves. Further, the processor 110 may determine whether a rotation is depicted in the video.

For example, when there is no main object present but only a sub object present in the video, the processor 110 may determine the video as a video of a first-person viewpoint. The main object may be an object, the size of which is larger than the sizes of the other objects. Further, the processor 110 may determine the video as a view of a first-person viewpoint when a rotation about the center point of the video is detected. After determining the video as a video of a first-person viewpoint, the processor 110 determines whether only the sub object moves or the background moves in the video. The processor 110 determines that it is unnecessary to apply an electrical stimulus signal when only the sub object moves, and determines that it is necessary to apply an electrical stimulus signal when the background moves. The main object may be an object situated at the center of the video and having a relatively small change of size, and the sub object may be an object situated in a periphery of the video and having a relatively large change of size.

Further, when the main object is fixed to the center of the video and the objects except for the main object move, the processor 110 determines the video as a video of a third-person viewpoint. Because relatively little sickness occurs when the user watches a video of a third-person viewpoint, the processor 110 may set an intensity of an electrical stimulus signal to be applied to the user when the user watches a video of a third-person viewpoint to be lower than an intensity of an electrical stimulus signal to be applied when the user watches a video of a first-person viewpoint. Further, the processor 110 may not apply an electrical stimulus signal when the user watches a video of a third-person viewpoint. The processor 110 may recognize an object based on a feature of the object by using a classifier built as a result of mechanical learning from the video. The processor 110 may use a pixel area approach scheme in which pixel data of a video is directly used, a compressed area approach scheme in which compressed view information is used, or a hybrid approach scheme in which the above-described schemes are combined.

In detail, the process 110 may extract a histogram of a local gradient (or in a direction of an edge) of the object in order to identify the object. Further, the processor 110 may detect an object by using a feature of the video calculated through various channels (an R, G, and/or B color value, a gray value, a gradient magnitude value, and a gradient histogram value) for a detection target area of the video.

The processor 110 may detect a border line of an object in the video. The processor 110 may detect a border line of an object by utilizing a color and a brightness of the video to determine a color difference and a brightness difference between adjacent pixels. For example, the processor 110 may detect an area having similar colors as one object. The processor 110 may connect points at which values representing the brightness of pixels change from a low value to a high value or from a high value to a low value to detect a border line of the object. The processor 110 may calculate a gradient by differentiating the pixel values of the video, and may detect points at which brightness changes by using the gradient.

The processor 110 may detect an area that includes a feature that is similar to the object model as an object. The processor 110 may extract key points from the video to compare the key points with the object model.

The processor 110 may detect a motion of an object. The processor 110 may detect a motion of the object based on a difference between a current frame and a previous frame.

The processor 110 may detect a motion of a video. The processor 110 may determine the same or similar blocks in the current frame and the previous frame, and may detect a motion depicted in the video based on movement of the same or similar blocks. The processor 110 may display a motion between the current frame and the previous frame by displaying the movement of the blocks as a vector.

The processor 110 may estimate a motion by using a block matching algorithm (BMA) or an optical flow. For example, the optical flow corresponds to a method of estimating a motion based on a difference between two sequential frames. The optical flow may represent how a brightness pattern has moved in a video. The optical flow may gradually change the brightness and display the direction and the speed of a motion in a video as a vector. A sparse optical flow corresponds to a method of extracting a main key point from a video and extracting motion information that corresponds to the extracted key point. A dense optical flow corresponds to motion information for respective pixels of a video, and a representative algorithm is a Gunner Farneback algorithm. A sparse optical flow may be used when a video that depicts a relatively large motion is analyzed, and a dense optical flow may be used when a video that depicts a relatively small motion is analyzed.

The processor 110 generates a signal for an electrical stimulus based on a motion depicted in a video. The processor 110 may generate a signal for an electrical stimulus when there is a motion depicted in a video itself rather than when there is a motion of the user wearing a video display apparatus.

The optical flow may be used for detecting an object and tracking a motion of the object.

Further, the processor 110 may detect portions constituting an object as well as the whole of the object, and may detect the object based on the whole and/or the portions of the object.

The processor 110 may detect the object by using the schemes, and may determine a viewpoint of the video based on the detected size and motion of the object.

As another example, the processor 110 may determine whether an electrical stimulus signal is to be applied, based on a change of pixels between the videos. The processor 110 determines whether a portion of the video is changed or the whole video is changed. The processor 110 may determine whether a portion of the video is changed by monitoring whether only pixels of a specific area of the video are changed. Further, the processor 110 may determine whether the whole video is changed by monitoring whether all the pixels of the video are changed or moved in parallel.

As another example, the processor 110 may determine whether an electrical stimulus signal is to be applied, based on a degree of change of the video. For example, the processor 110 may determine that an electrical stimulus signal is to be applied if the number of pixels for which corresponding pixel values are changed is not less than 50% of the number of all the pixels, and that an electrical stimulus signal is not to be applied if the number of pixels for which corresponding pixel values are changed is less than 50% of the number of all the pixels. The processor 110 may increase or decrease a ratio of the number of changed pixels to the number of all the pixels at the dictation of the user based on user preference.

The processor 110 generates a signal that is to be transmitted to the electrical stimulation apparatus 200. The processor 110 generates a signal based on a result of an analysis of the video. The processor 110 may generate a signal by determining an intensity, a frequency, a size, and an offset of an electrical stimulus.

The communication unit 130 is connected to the electrical stimulation apparatus 200 wirelessly or in a wired manner so as to transmit and receive a signal. The communication unit 130 may transmit and receive a signal via a short range communication such as Bluetooth or wireless fidelity (Wi-Fi) or other communication schemes. The communication schemes are not limited.

The display 120 provides a video for providing a virtual reality to a user. For example, the display 120 may display the same video in two divided screens such that the two eyes of the user 10 watch the same video.

Figure 4:
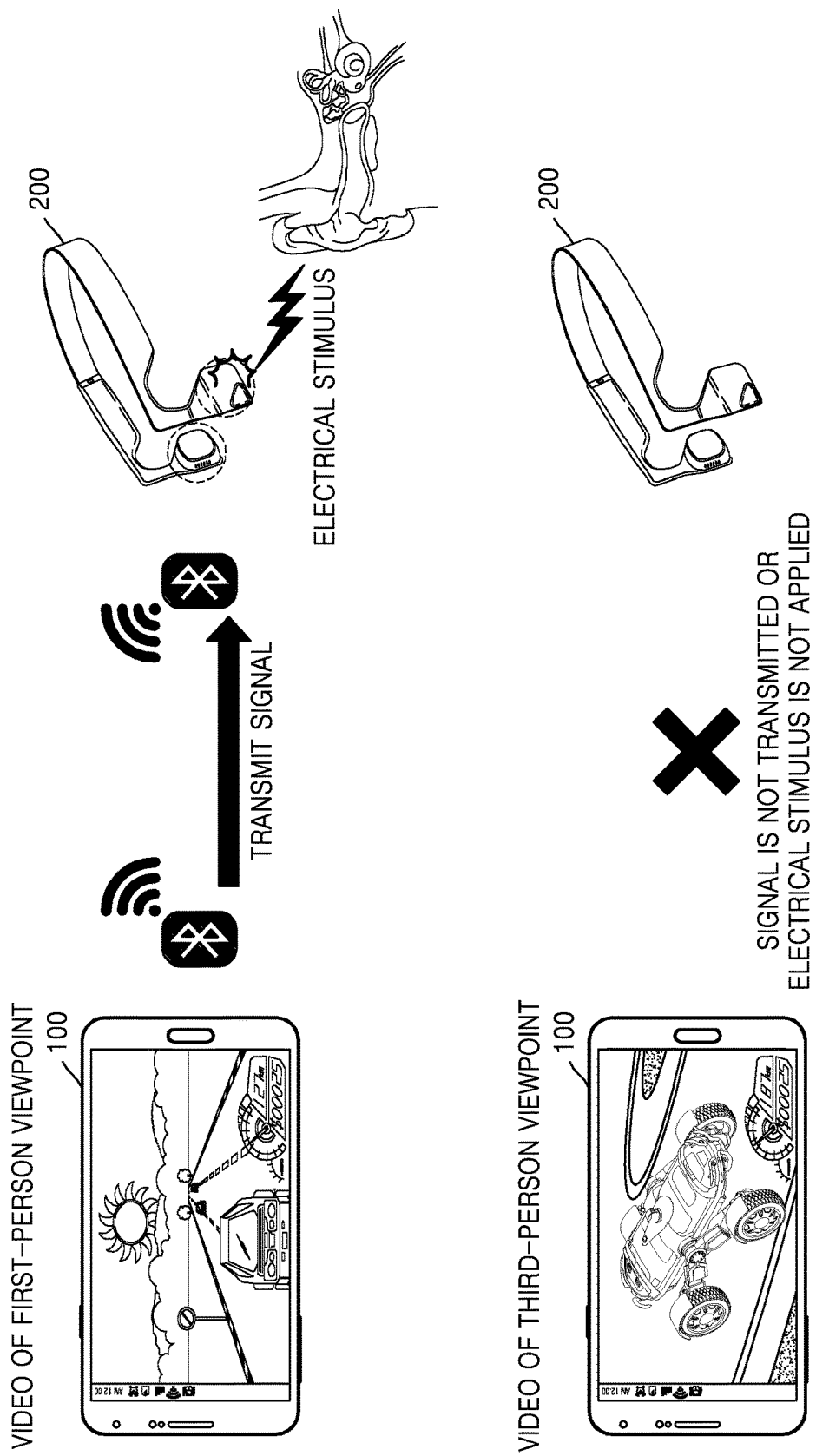
FIG. 4 is a diagram for explaining a method for applying an electrical stimulus based on a viewpoint of a video, according to an exemplary embodiment.

FIG. 4 is a diagram for explaining a method for applying an electrical stimulus based on a viewpoint of a video, according to an exemplary embodiment.

The video display apparatus 100 may determine whether an electrical stimulus is applied, based on a viewpoint of a video. The video display apparatus 100 transmits a signal for applying an electrical stimulus to the user to the electrical stimulation apparatus, based on a viewpoint of the video, or stops an operation of the electrical stimulation apparatus. For example, the video display apparatus 100 may determine whether a viewpoint of the video is a first-person viewpoint or a third-person viewpoint by analyzing the video.

If the viewpoint of the video is a first-person viewpoint, the video display apparatus 100 transmits a signal to the electrical stimulation apparatus 200 in order to control the electrical stimulation apparatus 200 such that the electrical stimulation apparatus 200 applies a signal to the user. A vehicle does not move in the video of a first-person viewpoint of FIG. 4, but a road is depicted as being in motion. When only objects move in the video of a first-person viewpoint, the video display apparatus 100 may not transmit a signal to the electrical stimulation apparatus 200. When objects do not or hardly move but the background is depicted as being in motion in the video of the first-person viewpoint, the video display apparatus 100 may transmit a signal to the electrical stimulation apparatus 200.

If the viewpoint of the video is a third-person viewpoint, the video display apparatus 100 does not transmit a signal to the electrical stimulation apparatus 200 or transmits a signal indicating that an electrical stimulus is not to be applied. As the electrical stimulation apparatus 200 is controlled by the video display apparatus 100, the electrical stimulation apparatus 200 does not apply an electrical stimulation to the user unless it receives a corresponding signal from the video display apparatus 100.

A vehicle moves in the video of a third-person viewpoint of FIG. 4, but a road may be still. The road may move together with the vehicle, depending on a video, but the road may appear to move less or in another pattern in the video of a third-person viewpoint as compared with the apparent movement of the road in a video of a first-person viewpoint.

Figure 5:
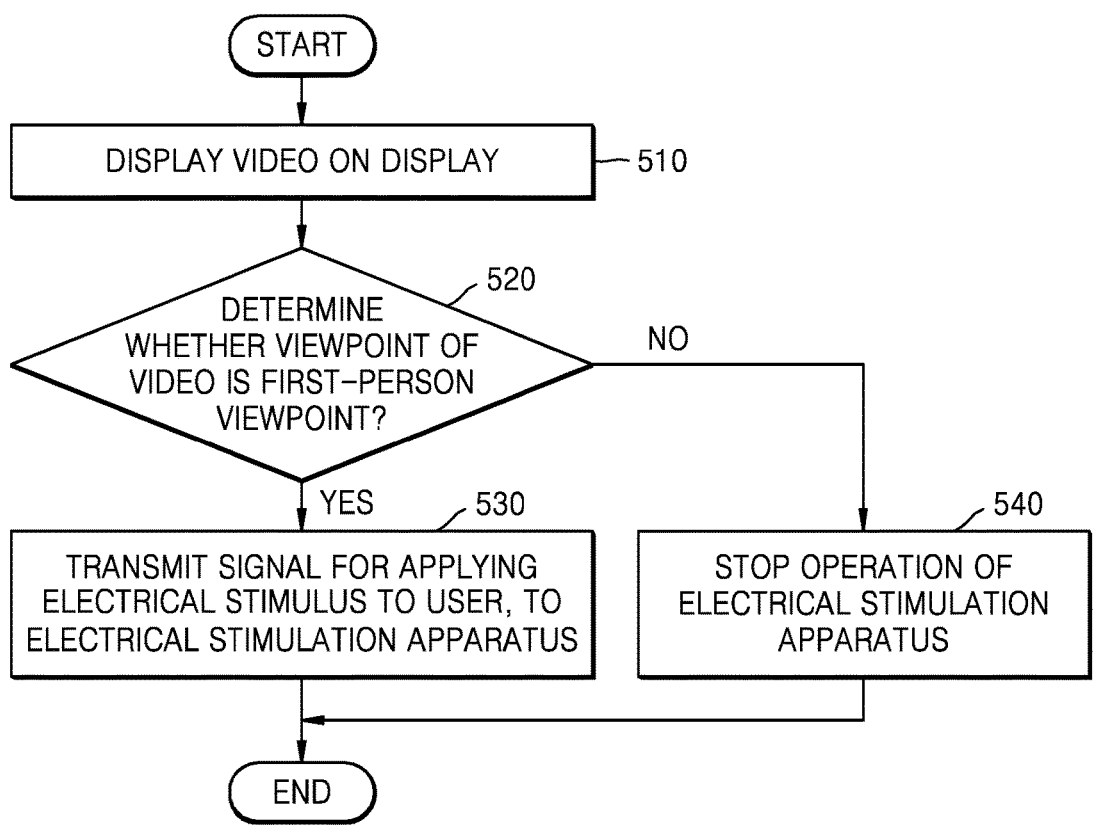
FIG. 5 is a flowchart illustrating the method for applying the electrical stimulus based on the viewpoint of the video, according to an exemplary embodiment.

FIG. 5 is a flowchart illustrating the method for applying an electrical stimulus based on a viewpoint of a video, according to an exemplary embodiment.

In operation 510, the video display apparatus 100 displays a video in the display 120.

In operation 520, the video display apparatus 100 determines whether the video corresponds to a first-person viewpoint. If the video corresponds to a first-person viewpoint, the operation proceeds to operation 530, and otherwise, the operation proceeds to operation 540.

In operation 530, the video display apparatus 100 transmits a signal for applying an electrical stimulus to the user, to the electrical stimulation apparatus 200.

In operation 540, the video display apparatus 100 stops an operation of the electrical stimulation apparatus 200.

Figure 6:
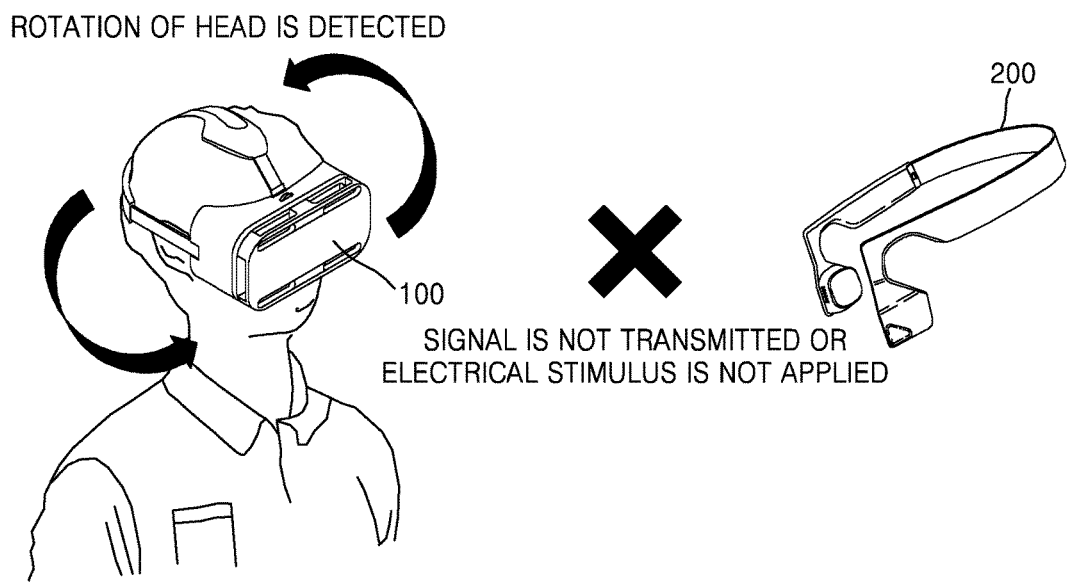
FIG. 6 is a diagram for explaining a method for controlling an electrical stimulation apparatus by the video display apparatus of FIG. 3.

FIG. 6 is a diagram for explaining a method for controlling an electrical stimulation apparatus by the video display apparatus. FIG. 6 illustrates a case in which the user rotates the head. While watching the video, the user may move the head. The video display apparatus 100 displays a video that varies based on a motion of the user. The head of the user may rotate leftwards or rightwards, or may rotate upwards or downwards. A rotation of the head of FIG. 6 means a case in which the user directly moves the head.

When detecting a rotation of the head of the user, the video display apparatus 100 controls the electrical stimulation apparatus 200 such that an electrical stimulus is not applied to the user. Because less visually induced motion sickness (VIMS) is caused while the video rotates as the head of the user rotates, the user may feel sicker if an electrical stimulus is applied to the user. Accordingly, the video display apparatus 100 does not transmit a signal to the electrical stimulation apparatus 200, or transmits a signal informing that an electrical stimulus is not to be applied.

When a motion is made by an external motion in conjunction with the user rotating, the video display apparatus 100 transmits a signal to control the electrical stimulation apparatus 200 such that an electrical stimulus is applied to the user. For example, when the user walks or is in a vehicle or on a train, the video display apparatus 100 controls the electrical stimulation apparatus 200 such that an electrical stimulus is applied to the user. The video display apparatus 100 may control the electrical stimulation apparatus 200 while distinguishing a case in which a motion of the user is made by an external motion while the user watches a video and a case in which a motion of the user is made by an external motion while the user does not watch a video.

When a motion is made by an external motion in conjunction with the user rotating, the electrical stimulation apparatus 200 transmits a signal to control the electrical stimulation apparatus 200 such that an electrical stimulus is applied to the user. For example, when the user walks or is in a vehicle or on a train, the user may feel sick. Then, the video display apparatus 100 or the electrical stimulation apparatus 200 may detect whether the user feels sick in real time, and may apply an electrical stimulus signal for reducing sickness to the user.

In another exemplary embodiment, a transportation means, such as a train or a hyper roof rail, moves along a fixed path. Accordingly, a region in which the user feels sick is in the path. The region in which the user feels sick may be determined by a location, a speed, and a directionality of the transportation means. A computer provided in the transportation means or a server connected to the transportation means may generate electrical stimulus data, based on the path, and the generated electrical stimulus data is transmitted to the video display apparatus 100 or the electrical stimulation apparatus 200.

In another example, the computer provided in the transportation means or the server connected to the transportation means may transmit a signal to the video display apparatus 100 or the electrical stimulation apparatus 200 based on electrical stimulus data in order to control the video display apparatus 100 or the electrical stimulation apparatus 200 such that the video display apparatus 100 or the electrical stimulation apparatus 200 applies an electrical stimulus signal to the user. The computer provided in the transportation means or the server connected to the transportation means detects a location of the user or the transportation means and determines whether it is an appropriate time to apply an electrical stimulus to the user. The computer provided in the transportation means or the server connected to the transportation means may transmit a signal to the video display apparatus 100 or the electrical stimulation apparatus 200 which the user wears, at a time point when an electrical stimulus is to be applied, so as to control the video display apparatus 100 or the electrical stimulation apparatus 200 such that the video display apparatus 100 or the electrical stimulation apparatus 200 applies an electrical stimulus signal to the user.

Figure 7:
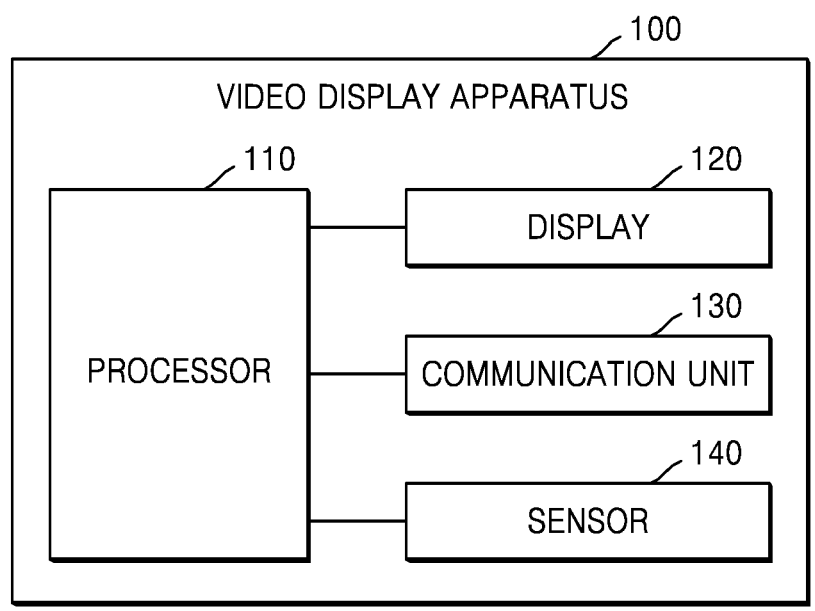
FIG. 7 is a block diagram illustrating a video display apparatus, according to an exemplary embodiment.

FIG. 7 is a block diagram illustrating a video display apparatus, according to an exemplary embodiment. The video display apparatus 100 of FIG. 7 further includes a sensor 140. The sensor 140 is a device that is configured for detecting a motion of the user. For example, the sensor 140 may include a motion sensor, such as a gyro sensor or an acceleration sensor.

The sensor 140 detects a motion of the user and outputs a detection result to the processor 110. The sensor 140 may detect a motion of the head, such as rotation, rolling, pitching, or yawing.

The processor 110 may determine whether an electrical stimulus is to be applied, based on the detection result received from the sensor 140. For example, when the sensor 140 detects that the head of the user rotates, the processor 110 may stop applying an electrical stimulus as described above with reference to FIG. 6.

Figure 8:
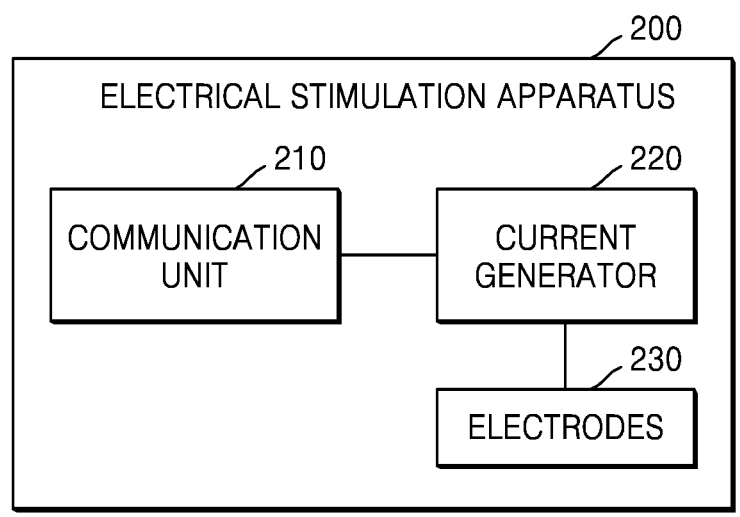
FIG. 8 is a block diagram illustrating an electrical stimulation apparatus, according to an exemplary embodiment.

FIG. 8 is a block diagram illustrating an electrical stimulation apparatus, according to an exemplary embodiment. Referring to FIG. 8, the electrical stimulation device 200 includes a communication unit (also referred to herein as a "communicator" and/or as a "transceiver") 210, a current generator 220, and a pair of electrodes 230.

The communication unit 210 is connected to the video display apparatus 100 by wire or wirelessly and configured to transmit and receive a signal. The communication unit 210 may transmit and receive a signal through short range communication, such as Bluetooth or Wi-Fi, or by using other communication schemes.

The communication unit 210 receives a signal that relates to an electrical stimulus from the video display apparatus 100, and outputs the received signal to the current generator 220.

The current generator 220 generates a current based on the signal received from the communication unit 210. The current generator 220 may adjust a magnitude and a frequency of the current. Further, the current generator 220 may add an offset to an AC current. The current generator 220 may determine an electrode 230 to which a current is to be applied, and a polarity, a magnitude, and the like of the current applied to the electrode 230, based on the signal received from the video display apparatus 100.

The electrodes 230 are attachable to the body of the user. The current flows to the body through the electrodes 230. Two electrodes 230 may be paired, and may be attached to rear sides of the ears of the user. Further, a pair of electrodes 230 may be attached to the vicinities of the temples of the user. Further, the electrodes 230 may be attached to the rear sides of the ears and the neck of the user, and the electrical stimulation apparatus 200 may cause a current to flow from the rear side of the left ear to the rear side of the neck, or from the rear side of the neck to the rear sides of the ears.

The attachment locations and number of the electrodes 230 are not limited thereto.

FIG. 9 is a graph for explaining an example of adjusting frequency based on a degree of change of a video. The video display apparatus 100 may determine frequency and current width according to a degree by which the video changes, and may transmit the determined frequency and current width to the electrical stimulation apparatus 200.

As the motion depicted in the video becomes greater, an electrical stimulus of a lower frequency and a larger current width may be applied to the user. In contrast, as the motion depicted in the video becomes smaller, an electrical stimulus of a higher frequency and a smaller current width may be applied to the user.

FIG. 9 illustrates a form of an electrical stimulus output by the electrical stimulation apparatus 200. The electrical stimulation apparatus 200 outputs a reference frequency signal to the electrodes 230 when an electrical stimulus based on a general motion is applied to the user. The electrical stimulation apparatus 200 outputs a relatively high frequency signal to the electrodes 230 when an electrical stimulus based on a relatively small motion is applied to the user. A high frequency means a frequency that is higher than the reference frequency. In contrast, the electrical stimulation apparatus 200 outputs a relatively low frequency signal, a frequency of which is lower than the reference frequency, to the electrodes 230 when an electrical stimulus based on a motion, which is greater than a general motion, is applied to the user.

FIG. 10 is a graph for explaining an example of adding an offset based on a rotational direction depicted in a video. The video display apparatus 100 may add an offset to an electrical stimulus based on a rotational direction depicted in the video. The video display apparatus 100 determines a direction of the offset based on a rotational direction, and transmits the determined direction of the offset to the electrical stimulation apparatus 200.

When the video depicts a leftward rotation, the video display apparatus 100 may add a negative offset. For example, the negative offset means that an AC current is moved to less than zero Amperes. In contrast, when the video depicts a rightward rotation, the video display apparatus 100 may add a positive offset. For example, the positive offset means that an AC current is moved to greater than zero Amperes.

Although FIG. 10 illustrates a direction of an offset based on a rotational direction depicted in a video, the direction of the offset may become opposite according to the location of an electrode, to which an electrical stimulus is applied.

The video display apparatus 100 may determine the size of the offset according to a change in direction. The video display apparatus 100 increases the size of the offset as the change in direction increases, and decreases the size of the offset as the change in direction decreases.

Figure 11:
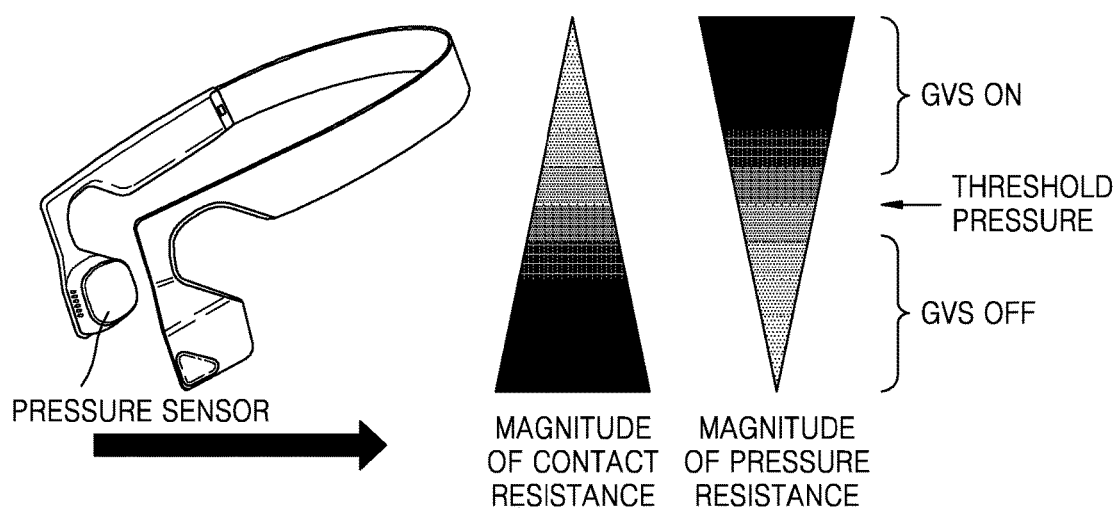
FIG. 11 is a diagram for explaining a method for determining an application of an electrical stimulus based on a degree of attachment of an electrode, according to an exemplary embodiment.

FIG. 11 is a diagram for explaining a method for determining an application of an electrical stimulus based on a degree of attachment of an electrode. A galvanic vestibular stimulation (GVS) system is an example of the electrical stimulation apparatus 200. The electrical stimulation apparatus 200 may or may not apply an electrical stimulus based on the magnitude of a pressure. Further, the electrical stimulation apparatus 200 may adjust an intensity of an electrical stimulus based on the magnitude of a pressure.

The electrical stimulation apparatus 200 may further include a pressure sensor. The pressure sensor may be attached to a rear surface of the electrode 230. The pressure sensor measures a pressure when the user wears the electrical stimulation apparatus 200. The electrical stimulation apparatus 200 transmits the measured pressure to the video display apparatus 100. A contact resistance and a pressure are inversely proportional to each other. Accordingly, the contact resistance decreases as the magnitude of the pressure increases, and the contact resistance increases as the magnitude of the pressure decreases. If the contact resistance is high, the user may feel uncomfortable because a relatively high voltage is applied even though the same current is output to the electrode 230. Accordingly, the electrical stimulation apparatus 200 adjusts the intensity of the electrical stimulus if the contact resistance is high (or the pressure is low), or does not apply an electrical stimulus if the pressure is lower than a threshold pressure.

The video display apparatus 100 controls the electrical stimulation apparatus 200 based on the magnitude of the pressure. The video display apparatus 100 stops an operation of the electrical stimulation apparatus 200 if the measured pressure is lower than the threshold pressure. That is, the video display apparatus 100 controls the electrical stimulation apparatus 200 such that an electrical stimulus is not applied to the user.

If the measured pressure is lower than the threshold pressure, the video display apparatus 100 informs the user of the fact. The video display apparatus 100 may display an alarm message via the display 120 or provide a sound. If the measured pressure is higher than the threshold pressure, the video display apparatus 100 may display a normal wearing message.

If the measured pressure is higher than the threshold pressure, the video display apparatus 100 prepares to apply an electrical stimulus. If the measured pressure is higher than the threshold pressure, this means that the user normally wears the electrical stimulation apparatus 200 and the electrodes 230 are properly attached to the user. Accordingly, the video display apparatus 100 transmits a signal for normally applying an electrical stimulus to the user, to the electrical stimulation apparatus 200. If the measured pressure is higher than the threshold pressure, the video display apparatus 100 adjusts the intensity of the electrical stimulus applied to the electrical stimulation apparatus 200 based on the magnitude of the pressure. Based on the contact resistance, the magnitude of a voltage actually applied to the user varies. Further, because the magnitudes of the contact resistances are different for the different users, the magnitude of the voltage felt by the users may vary even though the same voltage is applied. The electrical stimulation apparatus 200 may measure the magnitude of the voltage actually applied to the user. The electrical stimulation apparatus 200 may compare the magnitude of the voltage felt by the user with the magnitude of the voltage actually applied to the user in order to adjust the magnitude of the voltage applied to the user.

The electrical stimulation apparatus 200 may not output an electrical stimulus to the electrodes 230 if the electrical stimulation apparatus 200 receives a signal from the video display apparatus 100 or if the measured pressure is lower than the threshold pressure, even though the electrical stimulation apparatus 200 does not receive a signal.

Figure 12:
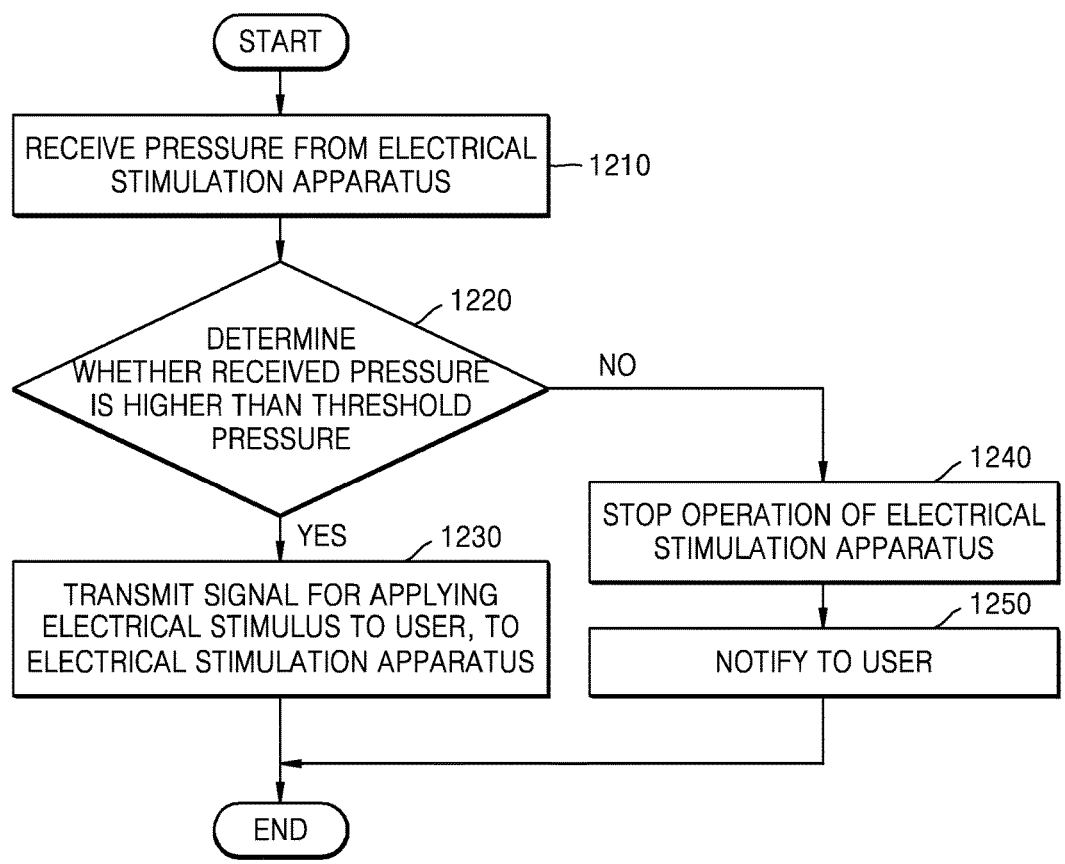
FIG. 12 is a flowchart illustrating a method for determining an application of an electrical stimulus based on a degree of attachment of electrodes, according to an exemplary embodiment.

FIG. 12 is a flowchart illustrating a method for determining an application of an electrical stimulus based on a degree of attachment of an electrode, according to an exemplary embodiment.

In operation 1210, the video display apparatus 100 receives a pressure measurement from the electrical stimulation apparatus 200.

In operation 1220, the video display apparatus 100 determines whether the received pressure is higher than the threshold pressure.

In operation 1230, the video display apparatus 100 transmits a signal for applying an electrical stimulus to the user, to the electrical stimulation apparatus 200. The video display apparatus 100 transmits a signal for applying an electrical stimulus to the user, to the electrical stimulation apparatus 200 only when the video corresponds to a first-person viewpoint.

In operation 1240, the video display apparatus 100 stops an operation of the electrical stimulation apparatus 200.

In operation 1250, the video display apparatus 100 notifies reports that the received pressure is lower than the threshold pressure. Further, the video display apparatus 100 may notify the user that an electrical stimulus is not applied. The video display apparatus 100 may display a message to the display 120 or may notify the user of the message by using a sound.

Figure 13:
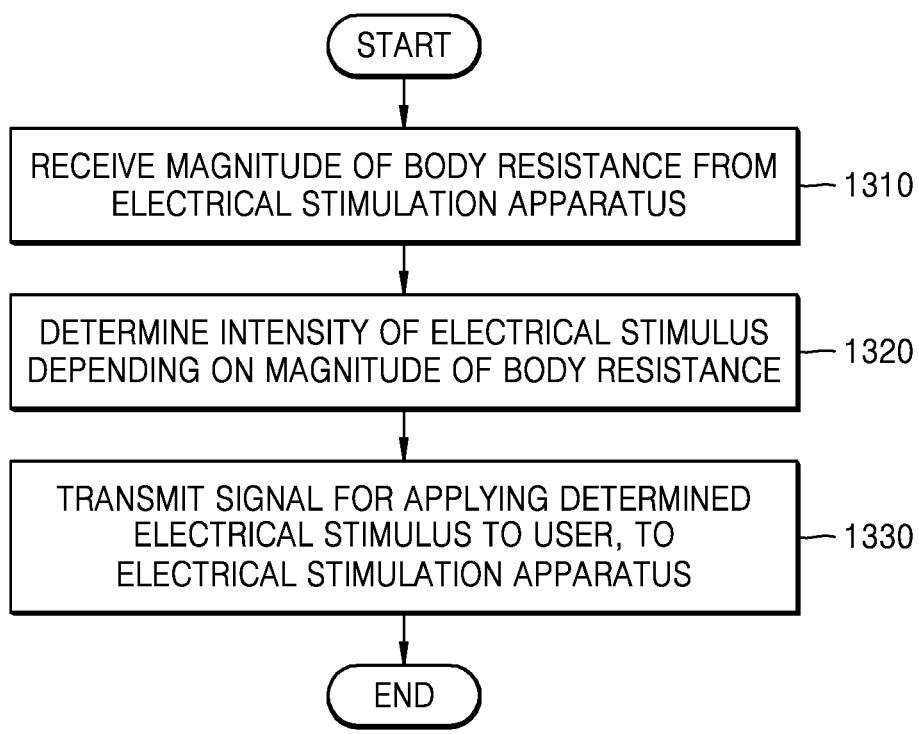
FIG. 13 is a flowchart illustrating a method for determining an application of an electrical stimulus based on a resistance of a human body, according to an exemplary embodiment.

FIG. 13 is a flowchart illustrating a method for determining an application of an electrical stimulus based on a resistance of a human body, according to an exemplary embodiment.

In operation 1310, the video display apparatus 100 receives a magnitude of a body resistance of the user from the electrical stimulation apparatus 200. The electrical stimulation apparatus 200 may apply a current to the body of the user and may measure a body resistance of the user by measuring a voltage.

In operation 1320, the video display apparatus 100 may determine an intensity of an electrical stimulus based on a magnitude of a body resistance of the user. Even though the same current is applied to the different users, it may cause inconvenience because voltages may differ between the users according to different body resistances.

In operation 1330, the video display apparatus 100 transmits a signal for applying the determined electrical stimulus to the user, to the electrical stimulation apparatus 200. The video display apparatus 100 may output the determined intensity of the electrical stimulus to the electrical stimulation apparatus 200.

The operations of FIG. 13 may be performed based on the premise that the viewpoint of the video is a first-person viewpoint and the electrodes 230 are properly attached to the user. In particular, only when the viewpoint of the video is a first-person viewpoint and the measured pressure is higher than the threshold pressure, may the video display apparatus 100 determine the intensity of the electrical stimulus based on the magnitude of the body resistance and apply an electrical stimulus to the user.

Further, the video display apparatus 100 may not apply an electrical stimulus to the user regardless of the viewpoint of the video, the magnitude of the pressure, the magnitude of the body resistance, and the like when the head of the user rotates.

Figure 14:
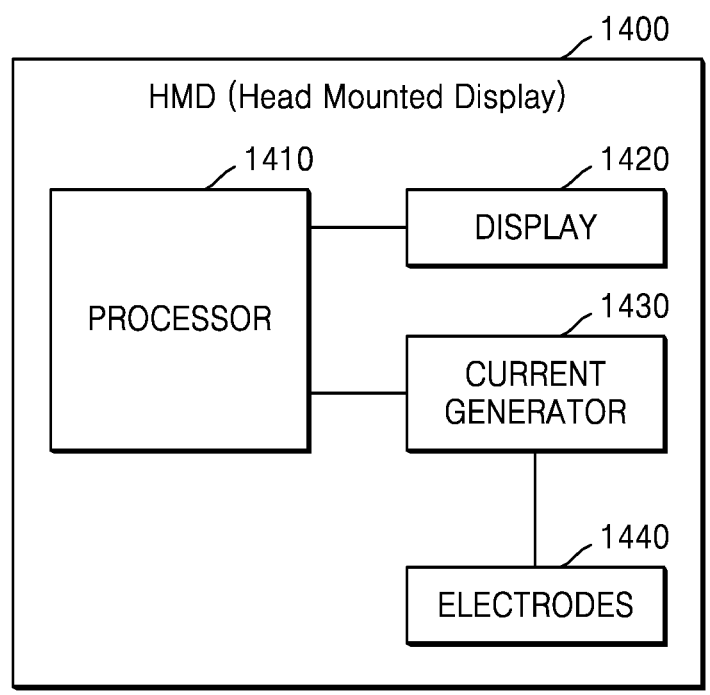
FIG. 14 is a block diagram of a head mounted display (HMD), according to an exemplary embodiment.

FIG. 14 is a block diagram of a head mounted display (HMD), according to an exemplary embodiment. The HMD 1400 of FIG. 14 may be a device in which the video display apparatus 100 and the electrical stimulation apparatus 200 are integrally manufactured. Accordingly, the HMD 1400 includes a processor 1410, a display 1420, a current generator 1430, and an electrode 1440, without including a separate communication unit. In addition, the HMD 1400 may further include any of an acceleration sensor, a gyro sensor, a pressure sensor, and/or a resistance measuring unit.

The description of the video display apparatus 100 and the electrical stimulation apparatus 200, which has been provided by the drawing, is also applied to the HMD 1400 of FIG. 14.

FIGS. 1 to 14 are views for explaining a method for reducing sickness of the user watching a virtual reality video, and FIGS. 15 to 19 are views for explaining a method for enhancing a sense of reality felt by the user watching a virtual reality video.

The user watches a motion depicted in a video, but feels sick because the body of the user does not actually move. Accordingly, the video display apparatus 100 stimulates vestibules, based on a motion depicted in the video, in order to reduce the sickness felt by the user watching a virtual reality video.

The user watching a virtual reality video may feel immersed as he or she feels the same motion as that depicted in the video. Accordingly, the video display apparatus 100 may enhance a sense of reality felt by the user, by enabling the user to feel the same motion as that depicted in the video by stimulating the vestibules in the same direction as that of the video and with the same intensity as that of the video. In order to enhance the sense of reality, electrical stimulus data is executed together with the video and an electrical stimulus is applied to the user, based on the electrical stimulus data. The electrical stimulus data includes a location of the body of the user to which an electrical stimulus is applied, and a time point and an intensity of the electrical stimulus.

The video display apparatus 100 may select a sickness reducing function and a reality enhancing function. The video display apparatus 100 selects the sickness reducing function only when the video is reproduced, and selects the reality enhancing function when the electrical stimulus data is executed together with the video. The video display apparatus 100 may select the sickness reducing function and the reality enhancing function, based on an input provided by the user.

The sickness reducing function is a function of applying an electrical stimulus to the user by analyzing the video in real time. When the sickness reducing function is selected, the electrical stimulus applied to the user may be an AC current. The video display apparatus 100 may change a magnitude, a frequency, an offset, and the like of the AC current.

The reality enhancing function is a function of adjusting the magnitude of the electrical stimulus data and the time point when the electrical stimulus is applied, by the video display apparatus 100. As the electrical stimulus data is created together with the video, the video display apparatus 100 applies an electrical stimulus, which is recorded in the electrical stimulus data, to the user. When the reality enhancing function is selected, the electrical stimulus applied to the user may be a signal based on a change of the video. The form and intensity of the electrical stimulus may be determined based on the change of the video.

Figure 15:
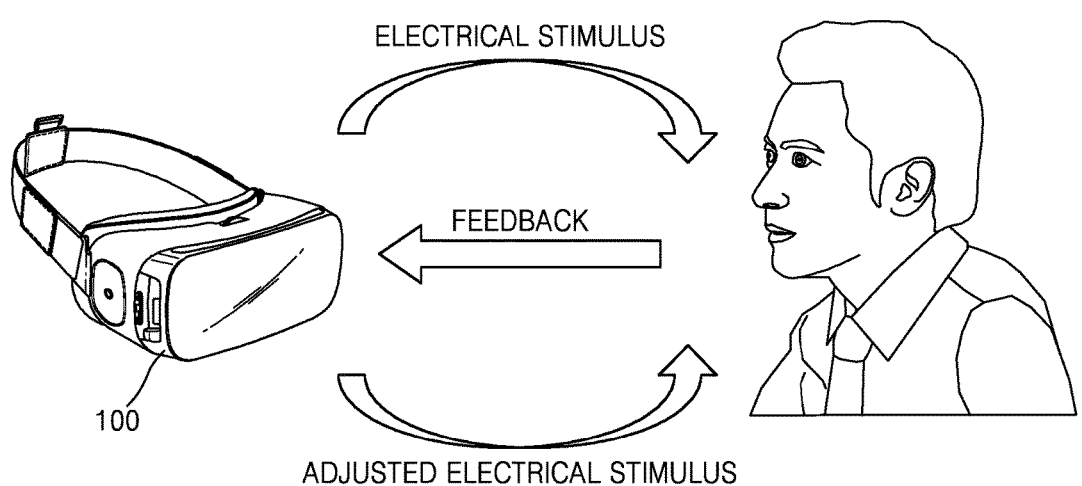
FIG. 15 is a diagram for explaining a method for adjusting an electrical stimulus, according to an exemplary embodiment.

FIG. 15 is a diagram for explaining a method for adjusting an electrical stimulus, according to an exemplary embodiment. The video display apparatus 100 may apply an electrical stimulus which is adjustable based on feedback from the user. In detail, the video display apparatus 100 adjusts the intensity of the electrical stimulus recorded in the electrical stimulus data.

The video display apparatus 100 applies an electrical stimulus to the user via the electrical stimulation apparatus 200. The video display apparatus 100 receives a feedback from the user. The feedback of the user may be received directly or indirectly from the user. For example, the user may directly adjust the intensity of the electrical stimulus. Further, the video display apparatus 100 may adjust an intensity of the electrical stimulus by detecting a motion of the user.

The video display apparatus 100 applies an electrical stimulus which is adjusted based on the feedback. The video display apparatus 100 may adjust an intensity of the electrical stimulus and a time point when the electrical stimulus is applied, based on the feedback. Further, the video display apparatus 100 may adjust the intensity or the time point without adjusting the form of the electrical stimulus.

Figure 16:
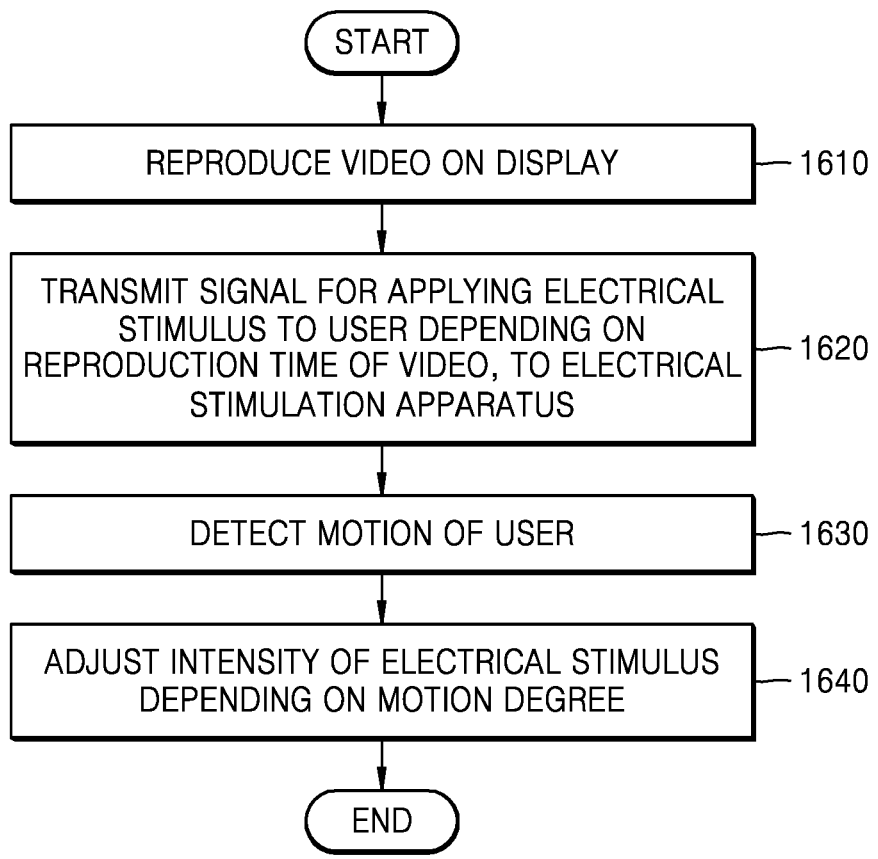
FIG. 16 is a flowchart illustrating a method for adjusting an intensity of an electrical stimulus by detecting a motion of the user, according to an exemplary embodiment.

FIG. 16 is a flowchart illustrating a method for adjusting an intensity of an electrical stimulus by detecting a motion of the user, according to an exemplary embodiment.

In operation 1610, the video display apparatus 100 reproduces a video on the display 120.

In operation 1620, the video display apparatus 100 transmits a signal for applying the electrical stimulus to the user, to the electrical stimulation apparatus 200, based on a reproduction time of the video. The video display apparatus 100 stores electrical stimulus data recording the form of the electrical stimulus, based on the reproduction time of the video. The electrical stimulus data is data created in advance based on a direction and a size of a motion depicted in the video. The electrical stimulus data may be executed together with a caption file if the video is reproduced. The video display apparatus 100 transmits a signal to the electrical stimulation apparatus 200, based on the electrical stimulus data.

In operation 1630, the video display apparatus 100 detects a motion of the user. The video display apparatus 100 may detect a motion of the user by using a motion sensor, such as, for example, a gyro sensor or an acceleration sensor.

In operation 1640, the video display apparatus 100 may adjust the intensity of the electrical stimulus, based on a motion degree of the user. The video display apparatus 100 may compare the intensity of the electrical stimulus recorded in the electrical stimulus data and the motion degree of the user in order to adjust the intensity of the electrical stimulus. For example, the video display apparatus 100 may decrease the intensity of the electrical stimulus if the motion of the user is relatively great as compared with the intensity of the electrical stimulus, and may increase the intensity of the electrical stimulus if the motion of the user is relatively small as compared with the intensity of the electrical stimulus. The video display apparatus 100 may compare the intensity of the electrical stimulus recorded in the electrical stimulus data and the motion degree of the user in order to update the sensitivity of the user, and may correspondingly adjust the intensity of the electrical stimulus. The sensitivity corresponds to values representing degree felt by different users for currents of the same magnitude. Even though the currents of the same magnitude are applied, the degrees felt by the user may vary. Accordingly, the video display apparatus 100 may update the sensitivity of the user, based on the motion degree of the user, and adjust the intensity of the electrical stimulus based on the updated sensitivity. In detail, the video display apparatus 100 may adjust only the magnitude of the current based on the sensitivity while maintaining the form of the electrical stimulus data.

Figure 17:
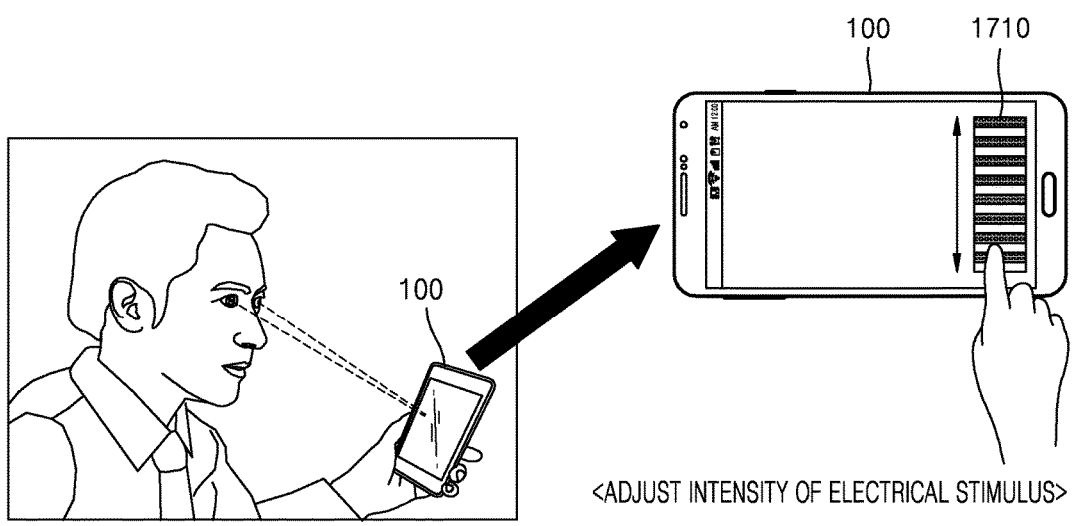
FIG. 17 is a diagram for explaining a method for adjusting an intensity of an electrical stimulus by the user, according to an exemplary embodiment.

FIG. 17 is a diagram for explaining a method for adjusting an electrical stimulus by the user, according to an exemplary embodiment.

The user may adjust an intensity of an electrical stimulus by using the video display apparatus 100. The video display apparatus 100 gradually increases the intensity of the electrical stimulus, and the user indicates a desired intensity of the electrical stimulus. The video display apparatus 100 applies an electrical stimulus based on the intensity of the electrical stimulus indicated by the user.

As illustrated in FIG. 17, the user may select a desired intensity of the electrical stimulus by touching a bar 1710 displayed on the display 120 of the video display apparatus 100. Further, the user may indicate the intensity of the electrical stimulus by using a physical button, such as a volume button, of the video display apparatus 100.

The video display apparatus 100 may indicate the intensity of the electrical stimulus by detecting a motion of the user even though there is not any direct input provided by the user. The video display apparatus 100 detects a motion degree of the user by using a motion sensor while the intensity of the electrical stimulus gradually increases. The video display apparatus 100 may adjust the intensity of the electrical stimulus based on the motion degree of the user as manifested with respect to the intensity of the electrical stimulus. The video display apparatus 100 may acquire a sensitivity of the user based on the motion degree of the user for the intensity of the electrical stimulus. The video display apparatus 100 sets a sensitivity of the user, and adjusts the intensity of the electrical stimulus based on the sensitivity.

Further, the video display apparatus 100 may select the intensity of the electrical stimulus by detecting a gesture of the user while the intensity of the electrical stimulus gradually increases. The user may indicate the intensity of the electrical stimulus by performing an operation of nodding his or her head or tapping an outside of the video display apparatus 100. The video display apparatus 100 may select an intensity of the electrical stimulus applied at a time point when a gesture of the user is detected as a reference intensity.

Figure 18:
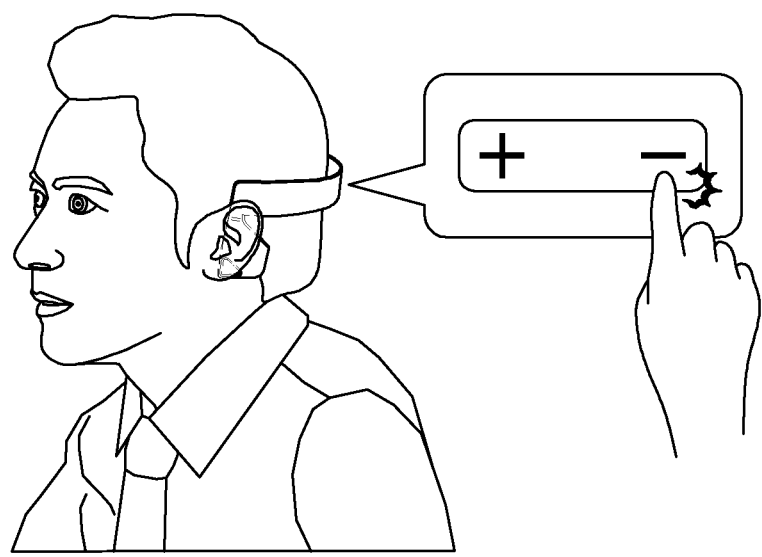
FIG. 18 is a diagram for explaining an example of adjusting an intensity of an electrical stimulus by using an electrical stimulation apparatus by the user, according to an exemplary embodiment.

FIG. 18 is a diagram for explaining an example of adjusting an intensity of an electrical stimulus by using an electrical stimulation apparatus by the user.

The electrical stimulation apparatus 200 may further include a physical button. The user may adjust the intensity of the electrical stimulus by pressing a button of the electrical stimulation apparatus 200. The user may increase or decrease the intensity of the electrical stimulus by pressing the button of the electrical stimulation apparatus 200 even while the video is reproduced.

The electrical stimulation apparatus 200 adjusts the magnitude of a current output to the electrodes 230, based on an input provided by the user. Further, the electrical stimulation apparatus 200 transmits the input provided by the user to the video display apparatus 100. The video display apparatus 100 may transmit a signal to the electrical stimulation apparatus 200, based on the input provided by the user.

Figure 19:
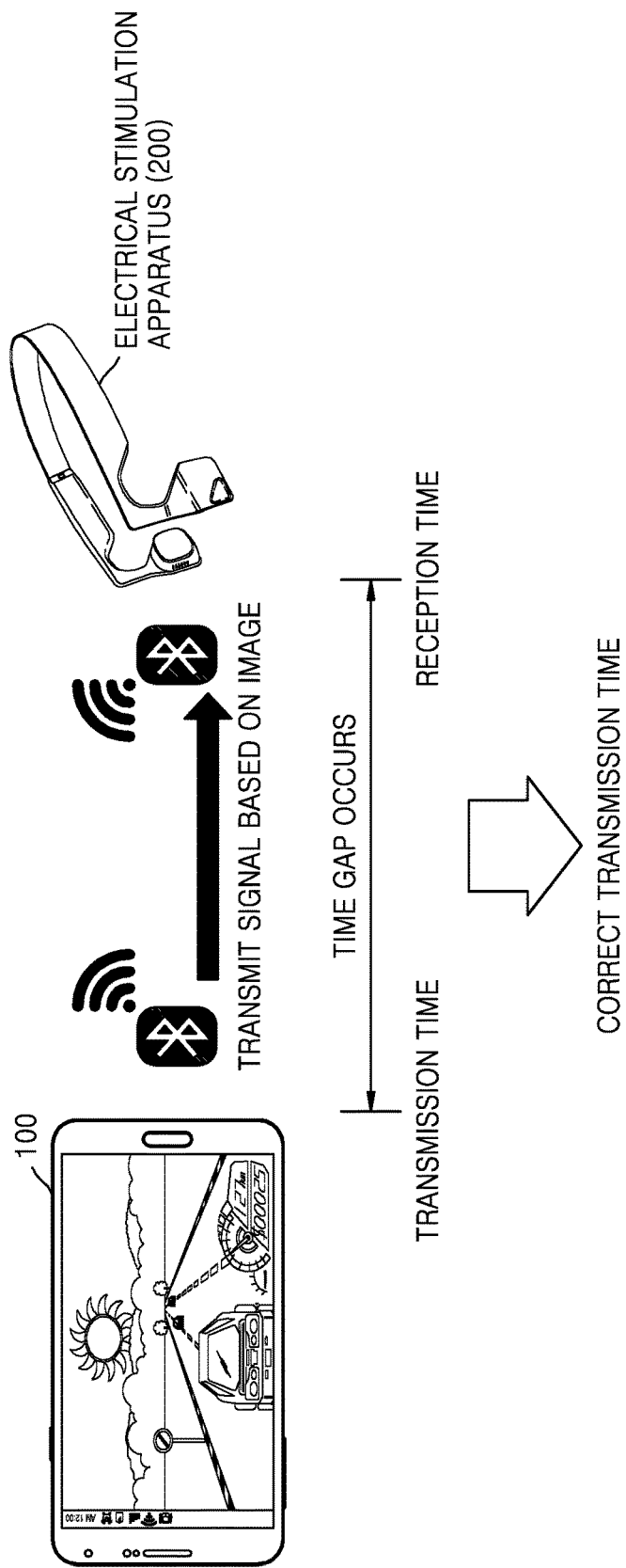
FIG. 19 is a diagram for explaining a method for correcting a transmission time of an electrical stimulus, according to an exemplary embodiment.

FIG. 19 is a diagram for explaining a method for correcting a transmission time of an electrical stimulus, according to an exemplary embodiment.

Because the video display apparatus 100 and the electrical stimulation apparatus 200 are connected to each other by wire or wirelessly, there occurs a gap (i.e., an interval of time) between a time point when the video display apparatus 100 transmits a signal and a time point when the electrical stimulation apparatus 200 receives the signal. Further, there is a gap between a time point when the video moves and a time point when the user feels an electrical stimulation.

The video display apparatus 100 is synchronized with the electrical stimulation apparatus 200 before the video is reproduced. The video display apparatus 100 transmits a signal to the electrical stimulation apparatus 200, and records a transmission time. The electrical stimulation apparatus 200 receives the signal, and records a reception time. The electrical stimulation apparatus 200 transmits the reception time to the video display apparatus 100. The video display apparatus 100 compares the transmission time with the reception time in order to adjust a signal transmission time. The signal transmission time is recorded in the electrical stimulus data together with a video that is to be reproduced. The video display apparatus 100 adjusts the signal transmission time recorded in the electrical stimulus data, and transmits a signal to the electrical stimulation apparatus 200 for the adjusted transmission time.

The video display apparatus 100 adjusts the signal transmission time based on a motion of the user. The video display apparatus 100 transmits a signal to the electrical stimulation apparatus 200, and records the signal transmission time. The video display apparatus 100 records a reaction time that is a time when the user reacts with an electrical stimulus. The video display apparatus 100 may detect a reaction of the user by using a motion sensor. The video display apparatus 100 compares the signal transmission time with the reaction time in order to adjust the signal transmission time.

The video display apparatus 100 may apply an electrical stimulus to the user at a time coinciding with a time when the video changes, by correcting the signal transmission time.

FIG. 20 is a table illustrating an example of electrical stimulus data representing video information. For example, the electrical stimulus data may in the form of meta data.

The video display apparatus 100 may store electrical stimulus data representing video information, together with a video. The electrical stimulus data is information that relates to an electrical stimulus signal to be applied to the user so as to reduce sickness and enhance a sense of reality while the video is reproduced.

For example, electrical stimulus data may include two fields of name and value. "Time" represents a time when an electrical stimulus is applied. "Type" represents a type of an electrical stimulus, and includes pitch, roll, and yaw. "Mode" represents a waveform of an electrical stimulus, and includes a direct current stimulus (DCS), an alternating current stimulus (ACS), and a custom motion type. "Current" represents a magnitude of a current. "Frequency" represents a frequency of an applied current. "Count" represents the number of repetitions of applied electrical stimuli. "Direction" represents a direction of an applied electrical stimulus.

The form of an electrical stimulus data of FIG. 20 is an example, and the electrical stimulus data may include various fields.

Figure 21:
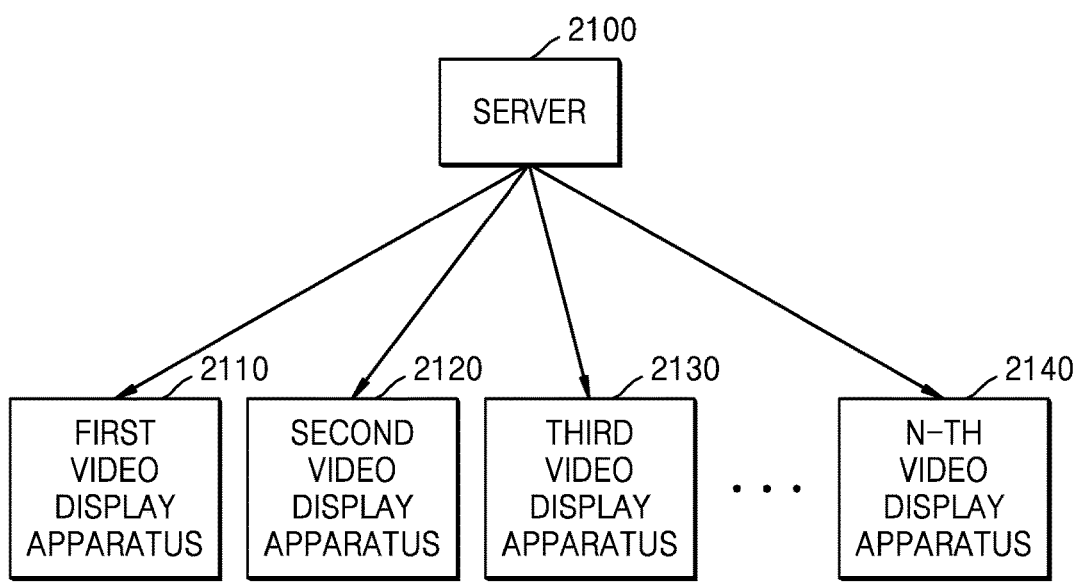
FIG. 21 is a view for explaining an example of transmitting an electrical stimulus signal or data from a server to a plurality of video display apparatuses, according to an exemplary embodiment.
Figure 22:
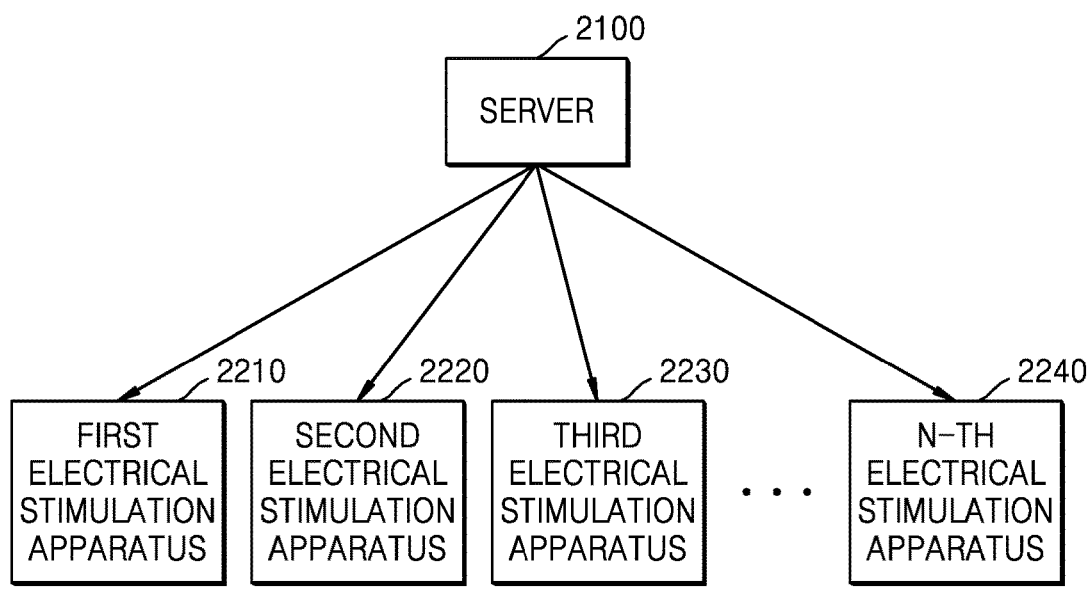
FIG. 22 is a view for explaining an example of transmitting an electrical stimulus signal or data from a server to a plurality of video display apparatuses, according to an exemplary embodiment.

FIGS. 21 and 22 are views for explaining an example of transmitting a signal to a plurality of video display apparatuses or electrical stimulation apparatuses by a server. The server 2100 may generate and store video data and electrical stimulus data. The electrical stimulus data includes information that relates to a time point when an electrical stimulus is applied, an intensity of the electrical stimulus, and a form of the electrical stimulus while video data is reproduced. The electrical stimulus data may be generated together with the video data while the video data is generated. For example, a movie manufacturer may manufacture electrical stimulus data that relates to a movie while manufacturing the movie.

The server 2100 transmits a signal to the plurality of video display apparatuses 2110, 2120, 2130, and 2140 or the plurality of electrical stimulation apparatuses 2210, 2220, 2230, and 2240. The plurality of video display apparatuses 2110, 2120, 2130, and 2140 or the plurality of electrical stimulation apparatuses 2210, 2220, 2230, and 2240 apply electrical stimuli to the user, based on the received signal.

As another example, the server 2100 may transmit video data or electrical stimulus data to the plurality of video display apparatuses 2110, 2120, 2130, and 2140 or the plurality of electrical stimulation apparatuses 2210, 2120, 2130, and 2240. The video display apparatuses 2110, 2120, 2130, and 2140 may apply electrical stimuli to the user based on the electrical stimulus data corresponding to the video data while the video data is reproduced. The video display apparatuses 2110, 2120, 2130, and 2140 apply an electrical stimulus recorded in the electrical stimulus data to the user based on a time point when the video is reproduced. The plurality of electrical stimulation apparatuses 2210, 2120, 2130, and 2240 may apply electrical stimuli to the user based on the electrical stimulus data.

FIG. 21 is a view for explaining an example of transmitting an electrical stimulus data or signal from a server to a plurality of video display apparatuses. The electrical stimulus data is data created to apply an electrical stimulus signal to the user based on a video, and may be transmitted to the video display apparatuses 2110, 2120, 2130, and 2140 before the video is reproduced. The signal is transmitted to the video display apparatuses 2110, 2120, 2130, and 2140 at a time point when an electrical stimulus is applied. The server 2100 transmits an electrical stimulus data or signal to the video display apparatuses 2110, 2120, 2130, and 2140, and the video display apparatuses 2110, 2120, 2130, and 2140 apply electrical stimuli to the user based on the electrical stimulus data or signal. The video display apparatuses 2110, 2120, 2130, and 2140 may reproduce a video corresponding to the received electrical stimulus data. If the video is reproduced, the video display apparatuses 2110, 2120, 2130, and 2140 search a memory to know whether electrical stimulus data corresponding to the reproduced video is stored. If the electrical stimulus data is found, the video display apparatuses 2110, 2120, 2130, and 2140 controls the electrical stimulation apparatus such that an electrical stimulus is applied, based on the electrical stimulus data, while the video is reproduced.

Although FIG. 21 illustrates that an electrical stimulus data or signal is transmitted to the video display apparatuses 2110, 2120, 2130, and 2140, the server 2100 may transmit an electrical data or signal to a plurality of HMDs.

FIG. 22 is a view for explaining an example of transmitting an electrical stimulus data or signal from a server to a plurality of video display apparatuses. The server 2100 transmits an electrical data or signal to the electrical stimulation apparatuses 2210, 2220, 2230, and 2240, and the electrical stimulation apparatuses 2210, 2220, 2230, and 2240 applies an electrical stimulus to the user based on the electrical stimulus data or signal. The server 2100 may transmit the electrical stimulus data or signal together with a video. Further, the server 2100 displays a video to a plurality of users, and transmits an electrical stimulus data or signal to the electrical stimulation apparatuses 2210, 2220, 2230, and 2240 such that the electrical stimulation apparatuses 2210, 2220, 2230, and 2240 worn by the users apply electrical stimuli to the users while the video is reproduced.

Hereinafter, a case in which many audiences enter a movie theater to watch a move will be exemplified. The audiences enter the movie theater and wear the electrical stimulation apparatus 2210 as if they wore 3D spectacles to watch a 3D movie. The server 2100 transmits an electrical stimulus data or signal to the electrical stimulation apparatus 2210 to apply the electrical signal to the audiences while the movie is reproduced. Because the audiences watch the same movie, the server 2100 may transmit the same electrical stimulus data to the plurality of electrical stimulation apparatuses 2210, 2220, 2230, and 2240, or may transmit a signal at the same time point.

Figure 23:
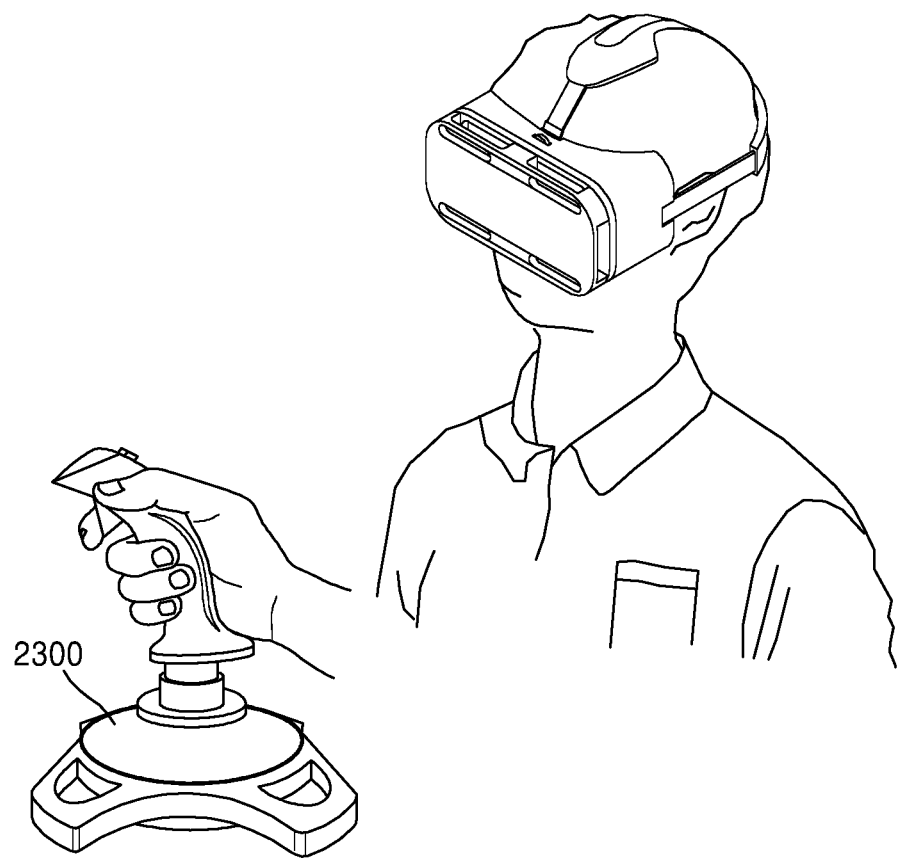
FIG. 23 is a diagram for explaining a method for manually applying an electrical stimulus signal by the user, according to an exemplary embodiment.

FIG. 23 is a diagram for explaining a method for manually applying an electrical stimulus signal by the user, according to an exemplary embodiment. Referring to FIG. 23, the user may manipulate a joystick 2300 based on a movement depicted in a video while watching the video. The joystick 2300 transmits a signal to the electrical stimulation apparatus 200 based on the manipulation of the user. The electrical stimulation apparatus 200 applies an electrical stimulus to the user based on the transmitted signal.

The user may manipulate the joystick 2300, and the electrical stimulation apparatus 200 may apply an electrical stimulus to the user according to a movement direction of the joystick 2300.

For example, the user may manipulate the joystick 2300 based on the motion depicted in the video in order to reduce sickness or enhance a sense of reality while watching the video. If the video depicts a leftward rotation, the user may rotate the joystick 2300 leftwards. If the video depicts a rightward rotation, the user may rotate the joystick 2300 rightwards. The user may directly control a direction, an intensity, and the like of the electrical stimulus signal by using the joystick 2300.

The joystick 2300 may include a ball and a stick, and the ball may be supported by the stick. The user may manipulate the ball, and the joystick 2300 may detect a motion of the ball and transmit a signal to the electrical stimulus apparatus.

As another exemplary embodiment, the user may attach a measurement apparatus for measuring a biometric signal of the user. The measurement apparatus may measure a biometric signal such as a pulse, a brain wave, or a body temperature of the user. Based on the measured biometric signal, it may be determined whether the user feels sick. The electrical stimulation apparatus 200 may reduce sickness by applying an electrical stimulus to the user, based on a signal output from the measurement apparatus.

Figure 24:
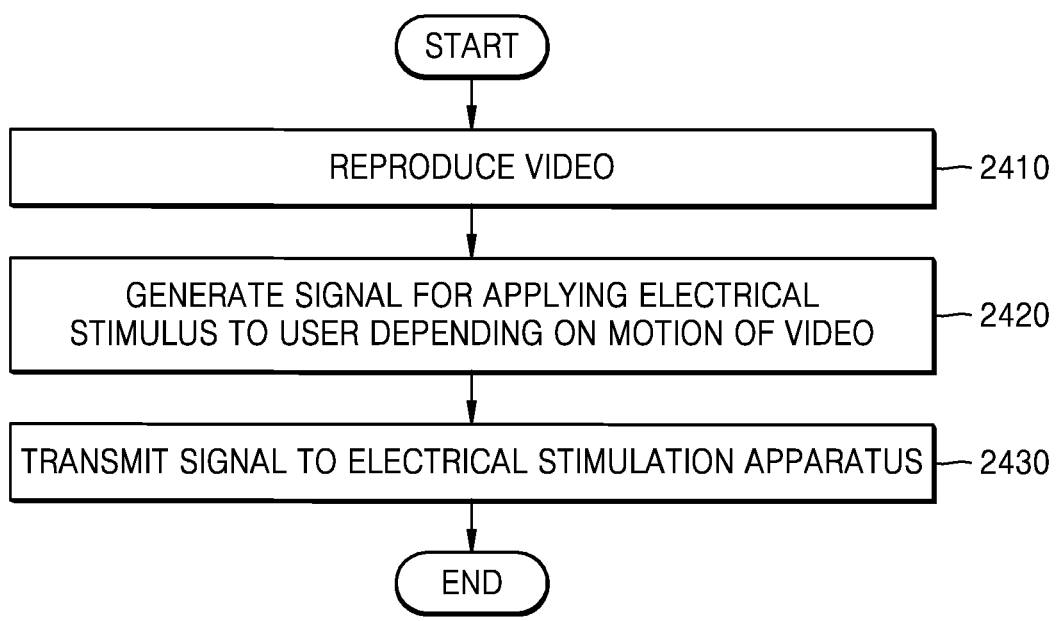
FIG. 24 is a flowchart for explaining a method for generating a signal for an electrical stimulus based on a motion of a video, according to an exemplary embodiment.

FIG. 24 is a flowchart for explaining a method for generating a signal for an electrical stimulus, based on a motion depicted in a video, according to an exemplary embodiment.

In operation 2410, the video display apparatus reproduces a video. The video may be a virtual reality video.

In operation 2420, the video display apparatus generates a signal for applying an electrical stimulus to the user, based on a motion depicted in a video. The video display apparatus detects a motion depicted in the video. The generated signal includes information, for example, that relates to an intensity of an electrical stimulus, a location of the body to which the electrical stimulus is applied, and a time point when the electrical stimulus is applied. The processor 110 may generate a signal for an electrical stimulus when not a motion of the user wearing a video display apparatus but a motion depicted in a video itself is made.

The video display apparatus may generate a signal based on a direction of a motion depicted in the video. The video may depict motions relating to any of being rotated, moved forwards, moved rearwards, enlarged, or reduced. The video display apparatus detects whether the video depicts a motion relating to being rotated, moved forwards, moved rearwards, enlarged, or reduced, and generates a signal based on the detected motion depicted in the video. The video display apparatus may detect a motion of the video by using a block matching algorithm (BMA) or an optical flow.

In operation 2430, the video display apparatus transmits a signal to the electrical stimulation apparatus. The electrical stimulation apparatus that receives the signal applies an electrical stimulus to the user based on the information contained in the signal.

The video display apparatus may generate a signal based on a viewpoint of the video. The viewpoint of the video may be a first-person viewpoint or a third-person viewpoint. The video display apparatus may generate a signal based on a motion depicted in the video when a video of a first-person viewpoint is reproduced. The video display apparatus may not generate a signal when a video of a third-person viewpoint is reproduced. Further, even when a video of a third-person viewpoint is reproduced, the video display apparatus may generate a signal representing an electrical stimulus of an intensity that is relatively low as compared with a case in which a video of a first-person viewpoint is reproduced.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by persons having ordinary skill in the art that various changes in form and details may be made therein without departing from the spirit and scope as defined by the following claims.

What is claimed is:

1. A video display apparatus comprising:
a display configured to reproduce a virtual reality video;
a processor configured to determine whether to generate a signal for applying an electrical stimulus to a user, based on a motion depicted in the video, and to generate the signal when a determination to generate the signal is made; and
a communicator configured to transmit the generated signal to an electrical stimulation apparatus,
wherein the processor is further configured to analyze the video and determine a viewpoint of the video based on the analyzed video, and
wherein the processor is further configured to:
generate the signal for applying the electrical stimulus to the user and control the communicator to transmit the signal to the electrical stimulation apparatus when the viewpoint of the video is determined to be a first-person viewpoint, and
generate a signal indicating that an electrical stimulus is not to be applied to the user and control the communicator to transmit the signal indicating that the electrical stimulus is not applied when the viewpoint of the video is determined to be a third-person viewpoint.

2. The video display apparatus of claim 1, wherein the processor is further configured to generate the signal for applying the electrical stimulus based on at least one from among a rotation, a forward movement, a rearward movement, an enlargement, and a reduction depicted in the video.

3. The video display apparatus of claim 1, further comprising:
a sensor configured to detect a motion of the user wearing the video display apparatus,
wherein the processor is further configured to adjust an intensity of the electrical stimulus, based on a degree of the detected motion of the user.

4. The video display apparatus of claim 3, wherein the processor is further configured to compare the intensity of the electrical stimulus with the degree of the detected motion of the user in order to update a sensitivity of the user, and to adjust the intensity of the electrical stimulus based on the updated sensitivity.

5. The video display apparatus of claim 3, wherein the display is further configured to display a depiction of the intensity of the electrical stimulus, to receive an input from the user, and to output the received input to the processor, and the processor is further configured to gradually increase the intensity of the electrical stimulus, and to adjust the intensity of the electrical stimulus to an intensity indicated by the user, based on the received input.

6. The video display apparatus of claim 3, wherein the processor is further configured to compare a time when the signal is transmitted with a time when the motion of the user is detected by the sensor in order to adjust a time when the electrical stimulus is transmitted.

7. The video display apparatus of claim 1, wherein the video having the first-person viewpoint corresponds to a video captured from a viewpoint of an object situated in a three-dimensional (3D) space, and the video having the third-person viewpoint corresponds to a video captured from an outside of the object situated in the 3D space.

8. A method for providing an electrical stimulus based on a virtual reality video, the method comprising:
reproducing the video;
determining whether to generate a signal for applying an electrical stimulus to a user, based on a motion depicted in the video;
generating the signal when a determination is made to generate the signal; and
transmitting the generated signal to an electrical stimulation apparatus,
wherein the method further comprises analyzing the video and determining a viewpoint of the video based on the analyzed video,
wherein the signal for applying the electrical stimulus to the user is generated and transmitted to the electrical stimulation apparatus when the viewpoint of the video is determined to be a first-person viewpoint, and
wherein a signal indicating that an electrical stimulus is not to be applied to the user is generated and transmitted to the electrical stimulation apparatus when the viewpoint of the video is determined to be a third-person viewpoint.

9. The method of claim 8, wherein the generating the signal comprises generating the signal for applying the electrical stimulus based on at least one from among a rotation, a forward movement, a rearward movement, an enlargement, and a reduction depicted in the video.

10. The method of claim 8, further comprising:
detecting a motion of the user wearing a video display apparatus,
wherein the generating the signal for applying the electrical stimulus comprises generating the signal for applying the electrical stimulus by adjusting an intensity of the electrical stimulus, based on a degree of the detected motion of the user.

11. The method of claim 10, wherein the adjusting the intensity of the electrical stimulus comprises comparing the intensity of the electrical stimulus with the degree of the detected motion of the user in order to update a sensitivity of the user, and adjusting the intensity of the electrical stimulus based on the updated sensitivity.

12. The method of claim 10, further comprising:
displaying a depiction of the intensity of the electrical stimulus; and
receiving an input from the user,
wherein the adjusting the intensity of the electrical stimulus comprises gradually increasing the intensity of the electrical stimulus and adjusting the intensity of the electrical stimulus to an intensity indicated by the user, based on the received input.

13. The method of claim 8, further comprising:
comparing a time when the signal for applying the electrical stimulus is transmitted with a time when the motion of the user is detected by a sensor, in order to adjust a time when the electrical stimulus is transmitted.

14. A non-transitory computer-readable recording medium in which a program for executing the method claimed in claim 8 by a computer is recorded.

15. The method of claim 8, wherein the video having the first-person viewpoint corresponds to a video captured from a viewpoint of an object situated in a three-dimensional (3D) space, and the video having the third-person viewpoint corresponds to a video captured from an outside of the object situated in the 3D space.

* * * * *